(12) United States Patent
Danek et al.

(10) Patent No.: US 11,925,207 B2
(45) Date of Patent: Mar. 12, 2024

(54) ELECTRONIC DEVICES FOR AEROSOLIZING AND INHALING LIQUID HAVING DIAPHRAGM AND A PRESSURE SENSOR

(71) Applicant: QNOVIA, INC., Richmond, VA (US)

(72) Inventors: Mario Danek, Austin, TX (US); Kassie Betts, San Diego, CA (US); Ian D. Kovacevich, Carlsbad, CA (US); Nouphone J. Bansansine, Temecula, CA (US); Joseph Gene Walsh, San Diego, CA (US); Christopher Kar-Heng Cheng, Portland, OR (US); Chris Breen, Clinton, MA (US); Josh Rigberg, Worcester, MA (US); Toriono Granger, Chicago, IL (US); Muawea Rawashdeh, St. Petersburg, FL (US); Ryan Hall, Holden, MA (US); Tonya Charles, Appleton, WI (US); Jacquelyn Coker, Nashua, NH (US)

(73) Assignee: QNOVIA, INC., Richmond, VA (US)

( * ) Notice: Subject to any disclaimer, the term of this patent is extended or adjusted under 35 U.S.C. 154(b) by 0 days.

(21) Appl. No.: 18/237,396

(22) Filed: Aug. 23, 2023

(65) Prior Publication Data
US 2023/0389605 A1 Dec. 7, 2023

Related U.S. Application Data

(63) Continuation of application No. 18/137,564, filed on Apr. 21, 2023.
(Continued)

(51) Int. Cl.
*A24F 40/42* (2020.01)
*A24F 40/05* (2020.01)
(Continued)

(52) U.S. Cl.
CPC .............. *A24F 40/42* (2020.01); *A24F 40/05* (2020.01); *A24F 40/10* (2020.01); *A24F 40/44* (2020.01);
(Continued)

(58) Field of Classification Search
CPC ........ A24F 40/42; A24F 40/46; A24F 40/485; A24F 40/10
See application file for complete search history.

(56) References Cited

U.S. PATENT DOCUMENTS

| 6,138,669 A | 10/2000 | Rocci, Jr. et al. |
| 7,013,894 B2 | 3/2006 | McFarland |

(Continued)

FOREIGN PATENT DOCUMENTS

| EP | 1154815 | 7/2004 |
| WO | 2021203038 A1 | 10/2021 |

(Continued)

OTHER PUBLICATIONS

"Innokin Adept: Unboxing Experience" (Kai's Virgin Vapor), Jul. 27, 2021, retrieved from https://web.archive.org/web/20210727211502/ https://www.kaisvirginvapor.com/pages/innokin-adept-unboxing-experience.

(Continued)

*Primary Examiner* — Hae Moon Hyeon
(74) *Attorney, Agent, or Firm* — TILLMAN WRIGHT, PLLC; Chad D. Tillman

(57) ABSTRACT

An electronic device includes a hand held base assembly that includes circuitry including memory and firmware executed by a processor or microcontroller of the circuitry; and a cartridge assembly that includes memory that is read by the firmware of the handheld base assembly. The cartridge assembly and the handheld base assembly are configured to removably couple together to define the electronic (Continued)

device for producing an aerosol for inhalation by a person. An enclosed air passageway is defined by the cartridge assembly and by the handheld base assembly, which isolates the airflow from the electronics of the device. The enclosed air passageway extends between the opening of the mouthpiece for taking a breath and a diaphragm of the handheld base assembly, movement of the diaphragm changing the air pressure within an enclosed interior space having a pressure sensor for trigging the pressure sensor when a breath is taken.

3 Claims, 41 Drawing Sheets

Related U.S. Application Data

(60) Provisional application No. 63/338,880, filed on May 5, 2022, provisional application No. 63/334,083, filed on Apr. 22, 2022.

(51) Int. Cl.
  *A24F 40/10*   (2020.01)
  *A24F 40/44*   (2020.01)
  *A24F 40/485*  (2020.01)
  *A24F 40/51*   (2020.01)
  *A24F 40/60*   (2020.01)
  *A24F 40/65*   (2020.01)
  *A24F 40/95*   (2020.01)
  *A61M 15/06*   (2006.01)

(52) U.S. Cl.
  CPC ............ *A24F 40/485* (2020.01); *A24F 40/51* (2020.01); *A24F 40/60* (2020.01); *A24F 40/65* (2020.01); *A24F 40/95* (2020.01); *A61M 15/06* (2013.01)

(56) References Cited

U.S. PATENT DOCUMENTS

| | | |
|---|---|---|
| 7,712,466 B2 | 5/2010 | Addington |
| 7,726,306 B2 | 6/2010 | Addington |
| 7,832,410 B2 | 11/2010 | Hon |
| 8,109,266 B2 | 2/2012 | Addington |
| 8,187,554 B2 | 5/2012 | Panagiotou |
| 8,336,545 B2 | 12/2012 | Fink |
| 8,555,874 B2 | 10/2013 | Fink |
| 8,616,195 B2 | 12/2013 | Power |
| 8,684,980 B2 | 4/2014 | Hunter |
| 8,910,625 B2 | 12/2014 | Mullinger |
| 9,022,027 B2 | 5/2015 | Addington |
| 9,220,294 B2 | 12/2015 | McCullough |
| 9,339,838 B2 | 5/2016 | Moran |
| 9,358,569 B2 | 6/2016 | Burt |
| 9,439,455 B2 | 9/2016 | Alarcon |
| 9,533,323 B2 | 1/2017 | Sauzade |
| 9,744,319 B2 | 8/2017 | Denyer |
| 9,757,528 B2 | 9/2017 | Rubin |
| 9,956,360 B2 | 5/2018 | Germinario |
| 10,076,140 B2 | 9/2018 | Silvestrini |
| 10,080,736 B2 | 9/2018 | Kleidon |
| 10,137,261 B2 | 11/2018 | Knudsen |
| 10,292,436 B2 | 5/2019 | Cirillo |
| 10,300,228 B2 | 5/2019 | Minskoff |
| 10,349,674 B2 | 7/2019 | Sur |
| 10,350,556 B2 | 7/2019 | Xiong |
| 10,531,687 B2 | 1/2020 | Liu |
| 10,548,349 B2 | 2/2020 | Sur |
| 10,561,803 B2 | 2/2020 | Liu |
| 10,609,962 B2 | 4/2020 | Zhu |
| 10,617,834 B2 | 4/2020 | Gould |
| 10,661,036 B2 | 5/2020 | McCullough |
| 10,667,559 B2 | 6/2020 | Bessant |
| 10,737,042 B2 | 8/2020 | Minskoff |
| 10,786,010 B2 | 9/2020 | Hubbard |
| 10,821,240 B2 | 11/2020 | McCullough |
| 10,856,572 B2 | 12/2020 | Sur |
| 10,857,313 B2 | 12/2020 | Fink |
| 10,888,117 B2 | 1/2021 | Danek |
| 10,918,127 B2 | 2/2021 | Fuisz |
| 11,039,641 B2 | 6/2021 | Liu |
| 11,077,261 B2 | 8/2021 | Liu |
| 11,247,003 B2 | 2/2022 | Rubin |
| 11,254,979 B2 | 2/2022 | Alshaiba |
| 11,317,476 B2 | 4/2022 | Schmidt |
| 11,325,149 B2 | 5/2022 | Tan |
| 11,458,267 B2 | 10/2022 | Hebrank |
| 11,478,019 B2 | 10/2022 | Qiu |
| 11,517,685 B2 | 12/2022 | Danek |
| 11,529,476 B2 | 12/2022 | Hunter |
| 11,558,934 B2 | 1/2023 | Ouyang |
| 11,653,152 B1 | 5/2023 | Lahoud |
| 11,665,483 B1 | 5/2023 | Lahoud |
| 11,666,713 B2 | 6/2023 | Lahoud |
| 11,672,928 B2 | 6/2023 | Lahoud |
| 11,690,963 B2 | 7/2023 | Danek |
| 11,730,191 B2 | 8/2023 | Lahoud |
| 11,730,193 B2 | 8/2023 | Lahoud |
| 11,785,985 B2 | 10/2023 | Lahoud |
| 2011/0226236 A1 | 9/2011 | Buchberger |
| 2013/0220315 A1 | 8/2013 | Conley et al. |
| 2014/0007874 A1 | 1/2014 | Ellwanger et al. |
| 2015/0238723 A1 | 8/2015 | Knudsen |
| 2016/0050976 A1 | 2/2016 | Righetti |
| 2016/0192708 A1 | 7/2016 | Demeritt |
| 2016/0213866 A1 | 7/2016 | Tan |
| 2016/0374397 A1 | 12/2016 | Jordan et al. |
| 2018/0043114 A1 | 2/2018 | Bowen et al. |
| 2019/0364957 A1* | 12/2019 | Fu ........................ A61M 11/042 |
| 2020/0060338 A1* | 2/2020 | Danek .................. A61M 15/06 |
| 2020/0120989 A1 | 4/2020 | Danek |
| 2020/0367553 A1* | 11/2020 | Hejazi ..................... A24F 40/48 |
| 2021/0113783 A1* | 4/2021 | Danek .................. A24B 15/283 |
| 2021/0177055 A1 | 6/2021 | Lahoud |
| 2021/0195947 A1 | 7/2021 | Lahoud |
| 2021/0282465 A1 | 9/2021 | Cristian |
| 2021/0402114 A1 | 12/2021 | Lahoud |
| 2022/0001121 A1 | 1/2022 | Lahoud |
| 2022/0040423 A1 | 2/2022 | Marmur |
| 2022/0132919 A1* | 5/2022 | Danek .................... A24B 15/42 |
| | | 131/329 |
| 2022/0132920 A1* | 5/2022 | Danek .................... A24F 40/42 |
| | | 131/275 |
| 2022/0132935 A1 | 5/2022 | Lahoud |
| 2022/0226587 A1 | 7/2022 | Hunter |
| 2022/0338535 A1 | 10/2022 | Danek |
| 2022/0370739 A1 | 11/2022 | Lahoud |
| 2022/0400745 A1 | 12/2022 | Lahoud |
| 2022/0400746 A1 | 12/2022 | Lahoud |
| 2023/0118045 A1 | 4/2023 | Danek |
| 2023/0121005 A1 | 4/2023 | Danek |
| 2023/0337735 A1 | 10/2023 | Danek |

FOREIGN PATENT DOCUMENTS

| | | |
|---|---|---|
| WO | 2023111495 A1 | 6/2023 |
| WO | 2023111496 A1 | 6/2023 |

OTHER PUBLICATIONS

"Biocompatibility of Medicinal Product Medical Device Combination for Airway Delivery" (Turner), May 17, 2021, retrieved from https://ondrugdelivery.com/biocompatibility-of-medicinal-product-medical-device-combinations-for-airway-delivery.

* cited by examiner

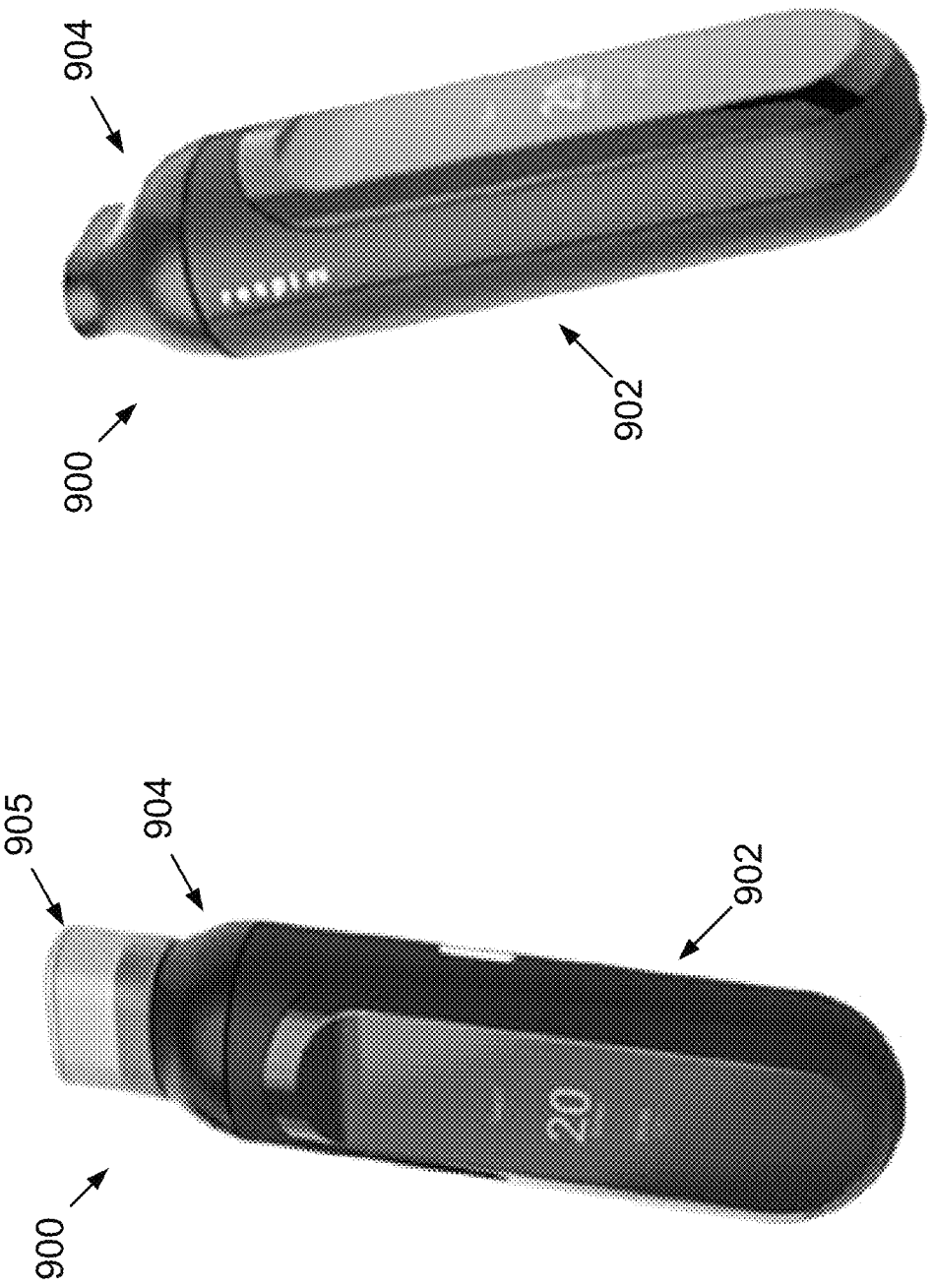

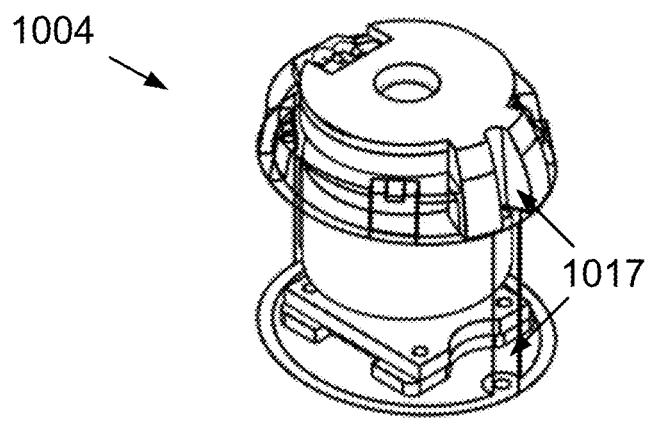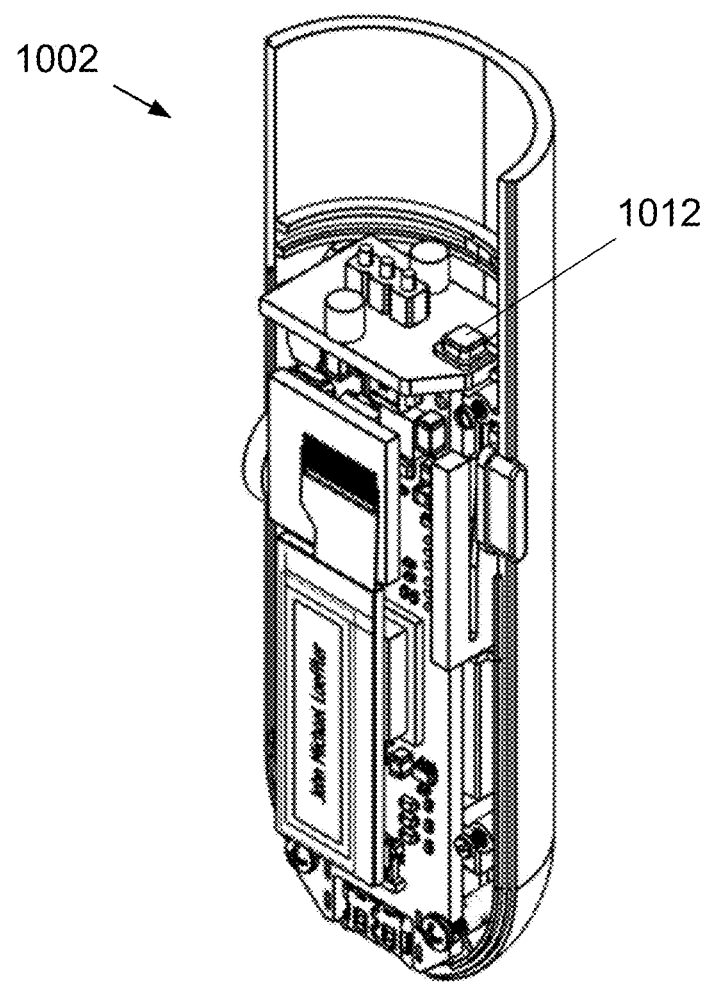
FIG. 13

WAVE Firmware Flow

Device is asleep – Push button to wake
　Wave logo fades onto display. Solid for 1 sec then fades to black > LogoDisplayTime
　DoseCount (doses in last 24 hours) count illuminates and stays solid for 5 seconds > DoseCountDisplayTime
　Device is ready to pair via BlueTooth
　　If successfully paired then display shows "PAIRED" for 1 second
　If no further action device goes back to sleep Device is awake
　Display is lit with dose count > DoseCount
　While awake Breath sense is waiting for breath
　If breath is sensed then mesh is activated for 3 seconds > MeshActiveTime
　When breath is sensed AND Haptic is ON (via app) then Haptic initiates based on HapticStart (Start, During, End) via app and
　　vibrates for 2 seconds > HapticActiveTime – Able to adjust via App
　Dose count updates (+1) and remains lit for DoseCountDisplayTime Device is awake and battery is low
　Display flashes "BATTERY"
　If connected to power then display shows "CHARGING"

Device is awake and has been locked via app
　Display shows "LOCKED"

Device is awake and Mouth piece not detected
　TotalDoses and DoseCount are reset to Zero
　Display shows "_ _"

Display is awake and looses paired device
　Device Display shows "LOST PAIR"
　App Alert alerts that "LOST PAIR"

FIG. 33

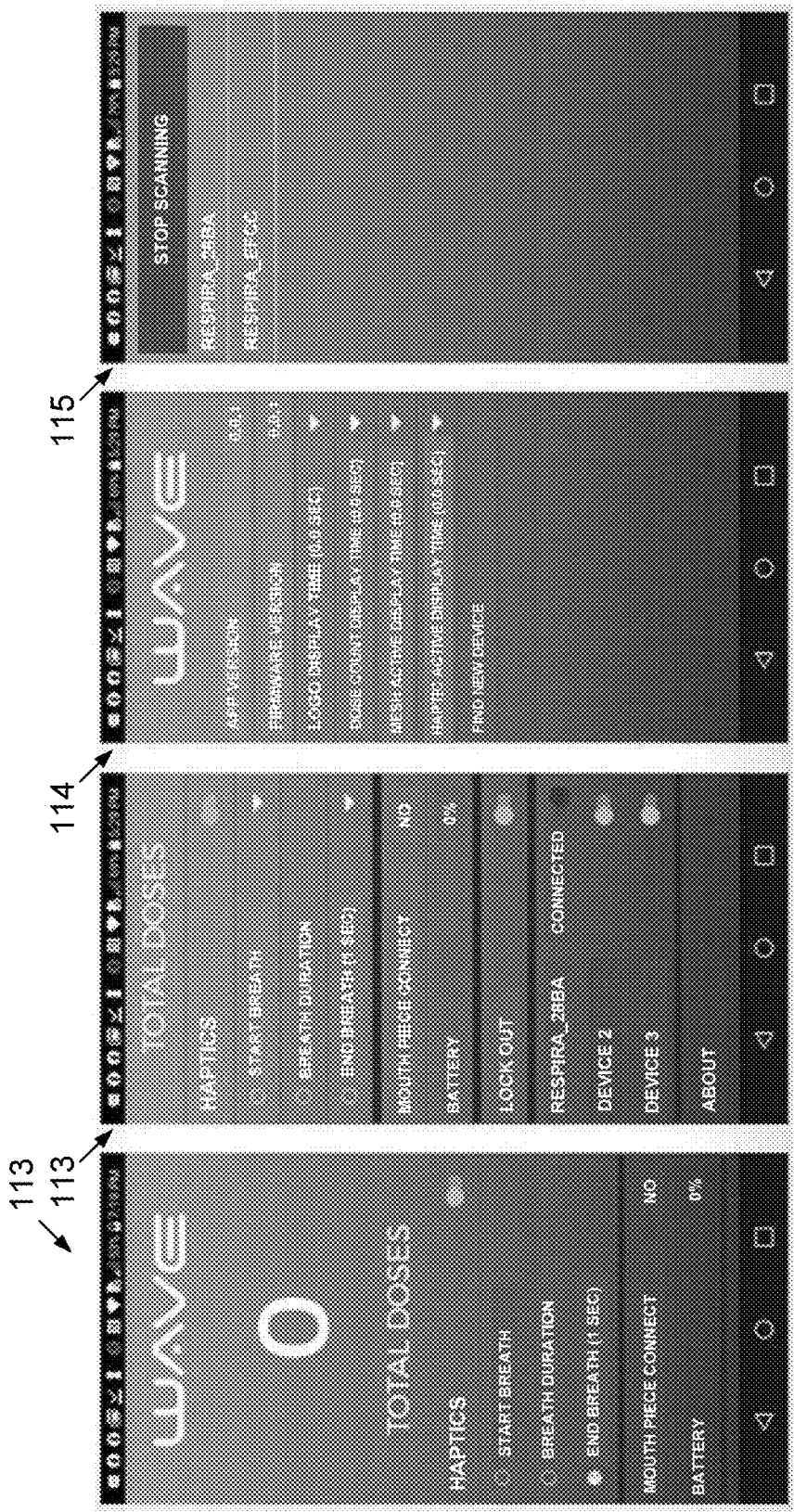

ELECTRONIC DEVICES FOR AEROSOLIZING AND INHALING LIQUID HAVING DIAPHRAGM AND A PRESSURE SENSOR

CROSS-REFERENCE TO RELATED APPLICATION

The present application incorporates by reference herein the disclosure of each of: U.S. Patent Application ("USPA") Ser. No. 17/075,679 filed Oct. 20, 2020; USPA Publ. US 2021/0113783 A1 representing the publication of the '679 application; USPA Ser. No. 17/518,572 filed Nov. 3, 2021; and USPA Publ. US 2022/0132920 A1 representing the publication of the '572 application. The present application further incorporates herein by reference USPA 63/334,083, filed Apr. 22, 2022; and USPA 63/338,880, filed May 5, 2022. Additionally, the appendix to the specification is incorporated herein by reference.

COPYRIGHT STATEMENT

Any new and original work of authorship in this document—including any source code—is subject to copyright protection under the copyright laws of the United States and other countries. Reproduction by anyone of this document as it appears in official governmental records is permitted, but otherwise all other copyright rights whatsoever are reserved.

INCORPORATION OF COMPUTER PROGRAM LISTING APPENDIX

Submitted concurrently herewith via the electronic filing system of the U.S. Patent & Trademark Office ("USPTO"), and incorporated herein by reference, is a computer program listing appendix representing computer program files including instructions, routines, and/or other contents of several computer programs. A table setting forth the name and size of files included in the computer program listing appendix is included below.

| File Name | Creation Date | File Size (bytes) |
|---|---|---|
| RESPIRA.TXT | 08/18/2023, 02:01 PM | 11405287 bytes |
| ASCIFY.TXT | 08/18/2023, 02:01 PM | 37473 bytes |
| README.TXT | 08/18/2023, 02:01 PM | 2890 bytes |
| DEVICE.TXT | 08/18/2023, 2:01 PM | 8298146 bytes |

One of these files, "readme.txt", contains instructions for extracting information from one or more other files of the computer program listing that represent a compressed binary file that has been converted to ascii format. These one or more other files can be converted back to a compressed .zip archive utilizing an assembly conversion program source code for which is contained in "ascify.txt". The "readme.txt" file includes instructions for compiling and running this conversion program, and instructions for converting the other one or more text files to a compressed, binary file. One compressed, binary file includes five electronic drawing files or "eDrawings" that collectively illustrate components of one or more embodiments in accordance with one or more aspects and features of the invention; another compressed, binary file contains one electronic drawing file or "eDrawings" that collectively illustrates an embodiment in accordance with one or more aspects and features of the invention. These eDrawing files can be opened using the free eDrawing viewer available from Dassault Systemes Solid-Works Corporation using a personal computer running a current version of the Windows operating system.

BACKGROUND OF THE INVENTION

The invention generally relates to apparatus, systems, and methods for producing an aerosol for inhalation by a person, whether intended for personal or recreational use, or more preferably, for the administration of medicines.

Vaping has been rapidly increasing in popularity, primarily because vaping provides a convenient, discreet, and presumably benign way to self-administer nicotine, *cannabis*, drugs, or other micronutrients. Indeed, there is a common belief that vaping is healthier than smoking cigarettes; vaping purportedly lets smokers avoid dangerous chemicals inhaled from regular cigarettes while still getting nicotine. Vaping also can be used for *cannabis*.

Vaping is performed using a vaporizer. A vaporizer includes a vape pen or a cigarette style vape, referred to by many as an e-cigarette or "eCig". A vape pen generally is an elongate, thin, and stylized tube that resembles a fancy pen. In contrast, an e-cigarette resembles an actual cigarette. The e-cigarette is usually small in size (usually smaller and more discreet than vape pens), easily portable, and easy to use.

A common vaporizer comprises a container, which may be a tank—which is typically refillable, or a cartridge—which is typically single-use and not refillable. The tank or cartridge holds a liquid often referred to as an e-liquid or e-juice. Tanks are made out of polycarbonate plastic, glass, or stainless steel. The vaporizer also includes a mouthpiece for inhaling by a person through the mouth; an atomizer comprising a tiny heating element that converts the liquid into tiny, airborne droplets that are inhaled; and a controller for turning on the atomizer. Many vape pens are mouth-activated and turn on automatically when a person inhales. Other vape pins are button activated and require the person to push a button to activate the atomizer. Vaporizers are electrically powered using one or more batteries. The batteries typically are lithium ion batteries that are rechargeable and primarily are used to heat the heating element of the atomizer. A charger usually accompanies a vaporizer when purchased for charging the batteries. The charger may be a universal serial bus ("USB") charger, car charger, or wall charger, and such chargers are generally similar to phone chargers.

The battery-powered vaporizer produces vapor from any of a variety of liquids and liquid mixtures, especially those containing nicotine or cannabinoids. Many different types and flavors are available. Moreover, the liquids can be non-medicated (i.e., containing no nicotine or other substances—just pure vegetable glycerin and flavoring), or the liquids can contain nicotine or even in some instances if and where legal, the liquids can contain tetrahydrocannabinol ("THC") and/or cannabidiol ("CBD"). The liquids also may contain one or more of a variety of flavors as well as micronutrients such as, for example, vitamin B12. A person can mix the liquids for use with a vape pen, and e-cigarettes typically are purchased with prefilled cartridges. The heating element in these devices turns the contents of the liquids into an aerosol—the vapor—that is inhaled into the lungs and then exhaled by the person. Perhaps one of the most popular vaporizers today is known as the "JUUL", which is a small, sleek device that resembles a computer USB flash drive.

It is believed that while promoted as healthier than traditional cigarette use, vaping actually may be more dangerous. Propylene glycol, vegetable glycerin and combinations or methylations thereof, are chemicals that are often mixed with nicotine, *cannabis*, or hemp oil for use in vaporizers. Propylene glycol is the primary ingredient in a majority of nicotine-infused e-cigarette liquids. Unfortunately, at high temperatures propylene glycol converts into tiny polymers that can wreak havoc on lung tissue. In particular, scientists know a great deal about propylene glycol. It is found in a plethora of common household items—cosmetics, baby wipes, pharmaceuticals, pet food, antifreeze, etc. The United States ("U.S.") Food and Drug Administration ("FDA") and Health Canada have deemed propylene glycol safe for human ingestion and topical application. But exposure by inhalation is another matter. Many things are safe to eat but dangerous to breathe. Because of low oral toxicity, propylene glycol is classified by the FDA as "generally recognized as safe" ("GRAS") for use as a food additive, but this assessment was based on toxicity studies that did not involve heating and breathing propylene glycol. Indeed, a 2010 study published in the International Journal of Environmental Research and Public Health concluded that airborne propylene glycol circulating indoors can induce or exacerbate asthma, eczema, and many allergic symptoms. Children were said to be particularly sensitive to these airborne toxins. An earlier toxicology review warned that propylene glycol, ubiquitous in hairsprays, could be harmful because aerosol particles lodge deep in the lungs and are not respirable.

Moreover, when propylene glycol is heated, whether by a red-hot metal coil of a heating element of a vaporizer or otherwise, the potential harm from inhalation exposure increases. It is believed that high voltage heat transforms the propylene glycol and other vaping additives into carbonyls. Carbonyls are a group of cancer-causing chemicals that include formaldehyde, which has been linked to spontaneous abortions and low birth weight. A known thermal breakdown product of propylene glycol, formaldehyde is an "International Agency for Research on Cancer" group 1 carcinogen!

Prevalent in nicotine eCig products and present in some vape oil cartridges, FDA-approved flavoring agents pose additional risks when inhaled rather than eaten. The flavoring compounds "smooth and creamy", i.e., diacetyl and acetyl propionyl, are associated with respiratory illness when inhaled in tobacco e-cigarette devices. Another hazardous-when-inhaled-but-safe-to-eat flavoring compound is Ceylon cinnamon, which becomes cytotoxic when aerosolized.

When a heating element gets red hot in a vaporizer, the liquid undergoes a process called "smoldering", which is a technical term for what is tantamount to "burning"; while much of the liquid is vaporized and atomized, a portion of the liquid undergoes pyrolysis or combustion. In that sense, most of the vaporizers that have flooded the commercial market may not be true vaporizers.

Additionally, clearance mechanisms of the lung, like all major points of contact with the external environment, have evolved to prevent the invasion of unwanted airborne particles from entering the body. Airway geometry, humidity and clearance mechanisms contribute to this filtration process.

In view of the foregoing, it is believed that a need exists for a vaporizer that provides an aerosol of the desired chemicals without the harmful byproducts that arise from smoldering. It is also believed that a need exists for a vaporizer that effectively and efficiently produces a vapor cloud that is not inhibited by the body's natural filtration process.

In the context of nicotine delivery through an aerosol, it is further believed that there is a need in developing nicotine-containing formulations in aqueous solutions that provides a user with an appealing sensorial experience. For example, at higher nicotine concentrations, the formulation is known to create a "harsh" sensorial experience for a user.

Furthermore, aspects and features of the invention also generally relate to apparatus, systems, formulations, and methods pertaining to liquids that are aerosolized and inhaled by persons using electronic devices, whether intended for personal or recreational use, or for the administration of medicines.

Indeed, inhalation delivery systems now play an increasing role in the targeted delivery of active ingredients to the human pulmonary system. This is true both for medical purposes, such as the targeted delivery of anti-cancer medications to the lungs, as well as for recreational/personal purposes, such as vaping, in which a liquid that includes the active ingredient is vaporized using heating so that the active ingredient can be inhaled into the human body.

Unfortunately, as inhalation delivery systems using heating have increased in prominence, concerns about their short and long term safety have come into focus. This is particularly true for vaping where there exist ongoing concerns about the possible presence of harmful and potentially harmful constituents ("HPHCs") in the inhaled vapor. Moreover, inhalation delivery systems are often unable to provide the desired effect to a user. This may be attributable to the pre-vaporized liquid becoming unstable over time or the active ingredient itself not being properly sized or dispersed for deposition in the alveolar lung.

Accordingly, a need exists for an active ingredient delivery system that enhances the shelf-life of the pre-vaporized liquid component and enhances the efficacy of the desired treatment/effect, while avoiding the presence of undesired HPHCs in the inhaled vapor. Each of these needs, and still other needs, are believed to be met by one or more embodiments in accordance with one or more aspects and features of the invention.

SUMMARY OF THE INVENTION

The invention includes many aspects and features. Moreover, while many aspects and features relate to, and are described in, the context of vaping, the invention is not limited to use only in such context. Indeed, a preferred context of use is in the delivery of medication and, in particular, prescription medication.

Depending on the context of use, the electronic device of the invention may be considered a vaporizer and may be in the form of a vape pen or e-cigarette. Indeed, those who vape may come to refer to embodiments of the invention as a vape pen even though heat is not utilized to create the aerosol that is inhaled. In the delivery of pharmaceuticals, patients may come to refer to embodiments of the invention as a nebulizer even though a gas transport (e.g., compressed gas) is not utilized and even though the aerosol that is produced in accordance with the invention may have a smaller particle size than the mist produced by common nebulizers. Other separate and distinct contexts of use of embodiments of the invention may similarly result in different nomenclature of the embodiments of the invention. "Electronic device" is used herein in reference to embodiments of the invention independent of context of use. Indeed, while the appearance and form factor of embodiments of the invention may vary depending on such contexts of use, the basic components and operation remain the same, except where otherwise described below.

In an aspect of the invention, a cartridge assembly is configured to couple with a handheld base assembly to form a portable, handheld electronic device. Preferably, the cartridge assembly and the handheld base are configured to magnetically couple. The handheld base assembly comprises electronics in the form of a printed circuit board and a power source in the form of a battery, which battery preferably is rechargeable. An electrical connection is made when the cartridge assembly is coupled with the handheld base assembly, by which the cartridge assembly is powered. The base also preferably includes magnets that magnetically attract a metal plate of the cartridge assembly to secure the cartridge assembly within an opening in an end of the base.

Additionally, in an aspect of the invention the handheld base assembly comprises circuitry including memory and firmware executed by a processor or microcontroller of the circuitry; and the cartridge assembly comprises memory (e.g., non-transitory computer-readable memory) that is read by the firmware of the handheld base assembly when executed by the processor. In a feature of this aspect, the firmware when executed by the processor further writes to the memory of the handheld base, to the cartridge assembly, or both to the memory of the handheld base, to the cartridge assembly.

In accordance with this aspect, the cartridge assembly comprises a cartridge and a bladder assembly contained within the cartridge. In turn, the bladder assembly comprises a bladder containing a wick and a mesh assembly that sits on top of and covers a mouth of the bladder. The wick acts to draw liquid to the mesh assembly. The wick is retained in physical engagement with the bladder proximate the bottom of the wick by protuberances that extend from the walls of the bladder. The protuberances may engage the bottom of the wick only, or may engage the wick along its longitudinal length between the bottom of the bladder and the mouth of the bladder. There preferably are three or four protuberances that symmetrically surround the wick in a discontinuous circular pattern and receive the wick in frictional fit therewith for maintaining axial alignment of the wick within the bladder along a central axis of the bladder. The wick extends from the bottom of the bladder to and is retained in abutting contact with the mesh assembly and, in particular, a piezoelectric disk having a mesh material which, when powered by the power source, vibrates so as to aerosolize a liquid contained within the bladder and wick.

In one or more embodiments, the mesh assembly is held in tension on top of a lip of the mouth of the bladder by a sealing O-ring that is forced into engagement with the mesh assembly by the attachment of a mouthpiece of the cartridge assembly to the cartridge. Screws are preferably utilized in effecting the attachment whereby the force by which the O-ring is held in contact with the mesh assembly may be adjusted. A spacer on a printed circuit board of the cartridge assembly may additionally engage the bottom of the silicone bladder and hold the wick in tension therethrough. Due to these features, it is believed that the bladder and wick ensure that the mesh remains in constant contact with the liquid for consistent aerosolization each time the electronic device is triggered. The liquid preferably is supplied to the vibrating mesh at a generally constant pressure whereby a generally uniform aerosol is produced, and this is accomplished regardless of the orientation of the electronic device.

In other embodiments, the mesh assembly sits on top of and is held in tension with the wick by being pressured along an annual area thereof by a piezo transducer which, in turn, sits on top of and is pressured along an annual area thereof against the mesh assembly by a pressure ring which, in turn, sits on top of and is pressured along an annual area thereof against the piezo transducer by a mouthpiece of the cartridge which, in turn, is secured to a lower body of the cartridge assembly in tensioned engagement with a top of the pressure ring. In alternative embodiments, contact with the mesh assembly by the wick may be intermittent rather than constant, with a very small gap or spacing appearing and disappearing between the mesh assembly and wick as the piezo oscillates out of phase with resultant oscillations of the wick. In this respect, a drumming occurs between the mesh assembly and the wick. Nonetheless, the liquid preferably is supplied to the vibrating mesh at a generally constant pressure whereby a generally uniform aerosol is produced, and this is accomplished regardless of the orientation of the electronic device.

In an aspect, the cartridge assembly comprises a printed circuit board or other electronics, and the cartridge assembly communicates with the handheld base assembly when coupled. Preferably, the printed circuit board of the cartridge assembly includes memory that includes information regarding the liquid contained in the bladder and dosing information related thereto, e.g., the number of doses dispensed so far from the cartridge assembly. The cartridge assembly further can be programmed to only work with one or more specified handheld base assemblies to the exclusion of other handheld base assemblies. For example, a cartridge assembly could be configured to work only with a handheld base assembly of a particular person, e.g., a certain patient for whom a prescription is provided via the cartridge assembly.

In a feature, the cartridge is disposable.

In a feature, the wick has a lengthwise channel that extends between its opposite ends. The channel assists in delivering liquid to the mesh assembly for aerosolizing. In an alternative feature, no lengthwise channel is provided in the wick.

In a feature, the wick is rigid.

In a feature, opening cross sections of the mesh that is in contact with the liquid is smaller than the opening cross section that faces the mouthpiece and exit of the aerosolized liquid. The taper angle and size of the perforated mesh preferably is adjusted via electro-forming methods to achieve a laminar and non-turbulent aerosol that is best suited for deep lung penetration and will, therefore, not yield large amounts of buccal deposition.

In a feature, an airflow channel is defined between an opening into the mouthpiece and a pressure sensor located within the handheld base assembly. A D-ring is provided to seal the interface between the cartridge and the mouthpiece to prevent loss of suction along the airflow channel. The airflow channel is defined by openings in the mouthpiece, the cartridge, the printed circuit board, the metal plate, and the chassis. One opening may be provided in connection with the mouthpiece; alternatively, three openings may be provided that are equally spaced around an O-ring.

In an alternative feature, an enclosed airflow passageway is defined from an opening of the mouthpiece to an opening of the handled base assembly. The enclosed air passageway is defined by the mouthpiece, the pressure ring, and the cartridge body of the cartridge assembly. Importantly, the air passageway so defined does not lead to any electronics or other components or materials of the cartridge assembly that would be considered harmful for human exposure. Instead, the air traveling through the enclosed airflow passageway is isolated from such harmful components and materials. Moreover, the portions of the mouthpiece, the pressure ring, and the cartridge body defining the enclosed air passageway are made from one or more materials classified not to be harmful to human exposure (such as silicone) the cartridge meets both medical device standards ISO 1093 and ISO 18562 for airpath requirements, wherein "ISO" stands for the International Organization for Standardization.

Similarly, the opening of the handheld base assembly leads to another air passage that is defined in the handheld base assembly and, preferably, that is defined within a wall of the handheld base assembly and that leads to a diaphragm that seals of the air passageway. The diaphragm also closes off an enclosed space on an opposite side of the diaphragm which includes a pressure sensor. Movement of the diaphragm affects a pressure within the enclosed space that triggers the pressure sensor.

A protuberance of the wall preferably define the opening into the air passageway of the cartridge assembly and extends to and, preferably, within by some extent the air passageway of the cartridge assembly, when the cartridge assembly and handheld base assembly are magnetically coupled together. A sealing member preferably is provided around the protuberance for sealing the connection between the air passageway of the cartridge assembly and the air passageway of the handheld base assembly.

Consequently, when a breath is drawn at the opening of the mouthpiece, a low pressure results at the diaphragm that causes a drop in pressure in the enclosed space, thereby triggering the pressure sensor in the handheld base assembly.

In order to avoid a drop in pressure that may overextend the diaphragm or otherwise cause damage, one or more additional openings into the enclosed air passageway extending through the cartridge assembly, the handheld base assembly, or both may be provided for serving as vents to reduce the pressure drop experienced at the diaphragm.

In other embodiments, the bladder is co-molded with a silicone bladder and another material providing rigidity. Such rigidity may be desired around the top and bottom of the bladder.

In an aspect, the bladder may be filled with the liquid by injection after assembly of the disposable cartridge assembly. The bladder preferably is made from a self-sealing silicone bladder, and when the injector needle is removed, the bladder re-seals and no liquid drains or leaks out. In this aspect, the liquid may be injected as a last stop via an access port/injector port that is located on the bottom of the cartridge. Alternatively, the bladder is inserted into the cartridge and then is filled with liquid first (top-down pour) without utilizing a needle or puncturing the bladder with an injector needle. In this manner, the bladder is filled by pouring liquid into the bladder and, once the desired volume has been dispensed, the wick is inserted inside the bladder and then the bladder is capped off by the mesh assembly and the rest of the disposable cartridge assembly is then assembled.

Alternatively, the bladder comprises a fill port adjacent a bottom area thereof through which a needle fills the bladder. A plug then may be inserted into the port for sealing fluid within the bladder. The fill port, the plug, or both may be made from silicone or another material.

In an aspect, an electronic device for producing an aerosol for inhalation by a person comprises a cartridge assembly and a handheld base assembly, wherein the cartridge assembly and the handheld base assembly are configured to removably couple together.

In a feature, the handheld base assembly comprises circuitry including firmware executed by a processor or microcontroller of the circuitry, and the cartridge assembly comprises memory that is read by the firmware of the handheld base assembly.

The cartridge assembly preferably comprises a mouthpiece; a cartridge assembly; and a bladder assembly. The bladder assembly preferably comprises a bladder; a wick contained within the bladder; and a mesh assembly. The mesh assembly preferably comprises a mesh material and a piezoelectric material, the mesh material being configured to vibrate when the piezoelectric material is actuated, whereby an aerosol is produced when the mesh material contacts a liquid of the bladder such that the aerosol may be inhaled through the mouthpiece.

In a feature, the cartridge assembly if disposable.

In a feature, the cartridge assembly and the handheld base assembly are configured to magnetically couple together.

In a feature, the disposable cartridge assembly magnetically mounts onto an end of the handheld base assembly.

In a feature, an enclosed air passageway is defined by the cartridge assembly and by the handheld base assembly, which isolates the airflow from the electronics of the device.

The enclosed air passageway extends between the opening of the mouthpiece for taking a breath. The handheld base assembly comprises a diaphragm, movement of the diaphragm changing the air pressure within an enclosed interior space having a pressure sensor for trigging the pressure sensor when a breath is taken on the mouthpiece, the pressure sensor in turn causing aerosolization to occur for administering a dose.

In another aspect, an electronic device for producing an aerosol for inhalation by a person comprises: (a) a cartridge assembly; and (b) a handheld base assembly. The cartridge assembly and the handheld base assembly are configured to removably couple together; the handheld base assembly comprises circuitry including firmware executed by a processor or microcontroller of the circuitry; and the cartridge assembly comprises memory that is read by the firmware of the handheld base assembly.

In a feature, the handheld base assembly comprises a display.

In a feature, a representation of doses provided using the electronic device from a particular cartridge assembly is identified through the display. The representation may comprise a number of doses provided, or a number of doses remaining in the particular cartridge assembly. Furthermore, a representation of a number of puffs in a said does is indicated through the display.

In a feature, when the handheld base assembly and the cartridge assembly are coupled together, firmware in memory of the handheld base assembly and executed by a processor or microcontroller of the circuitry of the handheld base assembly reads from a nonvolatile memory of the cartridge assembly a number of doses that have been dispensed from or that remain in the reservoir of the cartridge assembly.

In a feature, the handheld base assembly and the cartridge assembly are paired such that the cartridge assembly only works with the handheld base assembly with which it is paired by storing a unique identifier or other authenticating information in the cartridge assembly by which the firmware of the handheld base assembly is configured to authenticate the cartridge assembly. Preferably, said authenticating information is permanently stored in read-only memory of the cartridge assembly; and said pairing is performed at time of manufacture of the cartridge assembly and handheld base assembly, when a new cartridge assembly is first used with a handheld base assembly. Said authenticating information may be communicated to the handheld base assembly. The handheld base assembly may comprise a transceiver for wireless communications, and said authenticating information may be communicated to the handheld base assembly wirelessly over the Internet once the cartridge assembly to be used with the handheld base assembly is known, such as when a specific cartridge is prescribed using the specific cartridge assembly, or when a prescription is filled using the specific cartridge assembly.

In a feature, a battery of the electronic device is rechargeable using a USB port of the electronic device.

In a feature, the electronic device is configured to initiate a dosing when a button on an exterior of the electronic device is depressed for a predetermined period of time.

In a feature, the electronic device is configured to turn on when a button on an exterior of the electronic device is depressed for a predetermined period of time, and wherein the electronic device comprises a pressure sensor configured to detect when a breath is drawn from a mouthpiece of the cartridge assembly when the device is turned on and consequently cause aerosolization of a metered dose.

The pressure sensor preferably is contained within the handheld base assembly, and the cartridge assembly and handheld base assembly collective define an enclosed interior air passageway extending between an interior space of a mouthpiece of the cartridge assembly to the pressure sensor contained within and mounted to a circuit board of the handheld base assembly.

In a feature, the cartridge assembly comprises a mesh component is formed from 316L stainless steel.

Furthermore, the enclosed, interior air passageway is in fluid communication with the mesh assembly; the handheld base assembly comprises a diaphragm arranged proximate the pressure sensor by which a change in pressure is detected by the pressure sensor; no electronic components are exposed to the enclosed interior air passageway; and all components defining the enclosed interior air passageway are made from medical grade materials such that the electronic device is compliant with ISO 18562 and ISO 10993 standards.

In a feature, when the pressure sensor detects a breath, a haptic engine of the handheld base assembly is activated to provide sensory feedback to the user that a breath has been detected and that a dose is being aerosolized. The magnitude of the vibrations caused by the haptic engine and length of activation preferably are adjustable by a user through an app.

In a feature, the cartridge assembly comprises a vibrating mesh nebulizer stack defining a fully sealed airpath that is compliant with medical airpath ISO 18625 and medical device ISO 10993 standards.

In a feature, the cartridge assembly comprises a compliant, silicone bladder that interfaces with a mesh assembly to provide a liquid tight seal between an interior space of the bladder containing a liquid and a mesh of the mesh assembly for aerosolizing the liquid. The cartridge assembly preferably further comprises a pressure ring configured to apply circumferential pressure to a piezo assembly of the mesh assembly, the mesh assembly being sandwiched between the bladder and the pressure ring. A mouth of the bladder at a top of the bladder engages and forms a liquid seal with the mesh assembly, and the bladder comprises a fill port located on a bottom of the bladder for filling the bladder with a liquid. The bladder further comprises a plug for sealing the fill port after filling of the bladder with a liquid.

In a feature, the bladder has a capacity of 1.5 ml.

In another feature, the electronic device further comprises a sealing cap removably attached to the cartridge assembly in covering relation to a mouthpiece of the cartridge assembly.

In another feature, the handheld base assembly comprises a transceiver and the electronic device is configured to wirelessly communicate with an app on a smartphone, tablet device, or personal computer. The app preferably is configured to show a number of doses dispensed from a cartridge assembly coupled to the handheld base assembly.

In another aspect, commercial packaging comprises one of the electronic devices disclosed above. The handheld base assembly and the cartridge assembly of the electronic device preferably are separated from one another such that the electronic device requires assembly when removed from the commercial packaging, and the commercial packaging further comprises a charging cord and instructions for use.

In addition to the aforementioned aspects and features of the invention, it should be noted that the invention further encompasses the various logical combinations and subcombinations of such aspects and features. Thus, for example, claims in this or a divisional or continuing patent application or applications may be separately directed to any aspect, feature, or embodiment disclosed herein, or combination thereof, without requiring any other aspect, feature, or embodiment.

BRIEF DESCRIPTION OF THE DRAWINGS

One or more preferred embodiments of the invention now will be described in detail with reference to the accompanying drawings.

FIG. 1 is a schematic illustration of commercial packaging comprising a container 101 containing an electronic device 100 for producing an aerosol for inhalation by a person in accordance with one or more aspects and features of the invention, wherein a handheld base assembly 102 and a cartridge assembly 104 of the electronic device 100 are shown as separated, individual components together with a cap 103, USB charging cord 105, and instructions for use (IFU 107, which itself is illustrated in FIG. 47).

FIG. 2 is a perspective view of the preferred electronic device 100 of FIG. 1 and indicates the removable coupling together of the handheld base assembly 102 and the cartridge assembly 104.

FIG. 3 illustrates a perspective view of the electronic device 100 when the handheld base assembly 102 and the cartridge assembly 104 are removably coupled together. As shown in FIG. 3, a number of doses is displayed on a display 106 of the electronic device 100, which indicates how many doses have been metered by the device (or one like it) from a reservoir of the specific cartridge assembly 104.

FIG. 4 illustrates a perspective view of another electronic device 900 for producing an aerosol for inhalation by a person in accordance with one or more aspects and features of the invention, wherein when a handheld base assembly 902 and a cartridge assembly 904 with a sealing cap 905 are removably coupled together.

FIG. 5 is another view of the electronic device 900 with the sealing cap 905 removed to expose an opening of a mouthpiece of the cartridge assembly 904.

FIG. 6 is a side elevational view in partial transparency of the electronic device 900.

FIG. 7 is an exploded view of the handheld base assembly 902 of the electronic device 900.

FIG. 8 is an exploded view of the cartridge assembly 904 of the electronic device 900.

Figure 12:
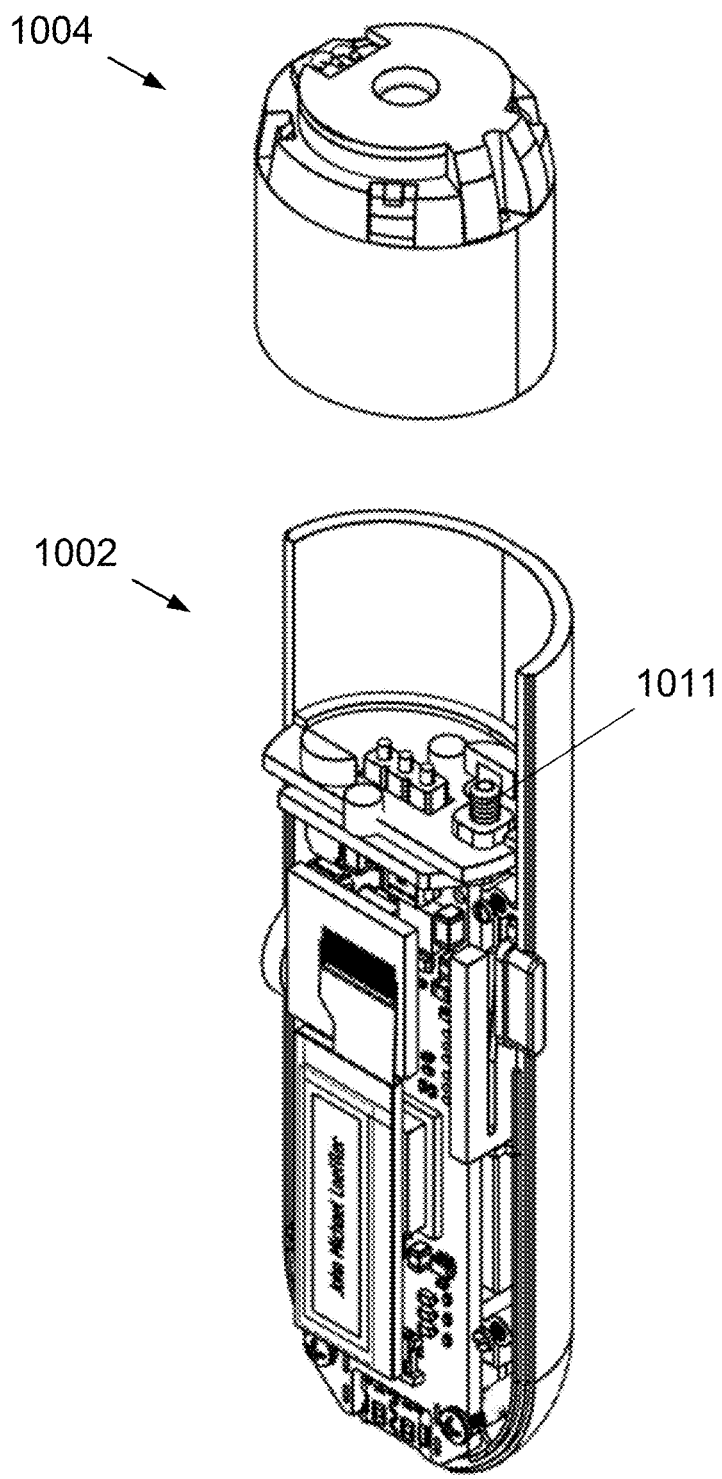

FIG. 12 is a view illustrating one or more components of the handheld base assembly 1002 and one or more components of the cartridge assembly 1004 of the electronic device 1000, wherein a protuberance 1011 defined by a wall of the handheld base assembly 1002 is seen, the protuberance defining in part the enclosed air passageway to a diaphragm 1012 of the handheld base assembly 1002 (perhaps best seen in FIG. 13).

FIG. 13 is a view illustrating one or more components of the handheld base assembly 1002 and one or more components of the cartridge assembly 1004 of the electronic device 1000, wherein the diaphragm 1012 is perhaps best seen.

Figure 14:
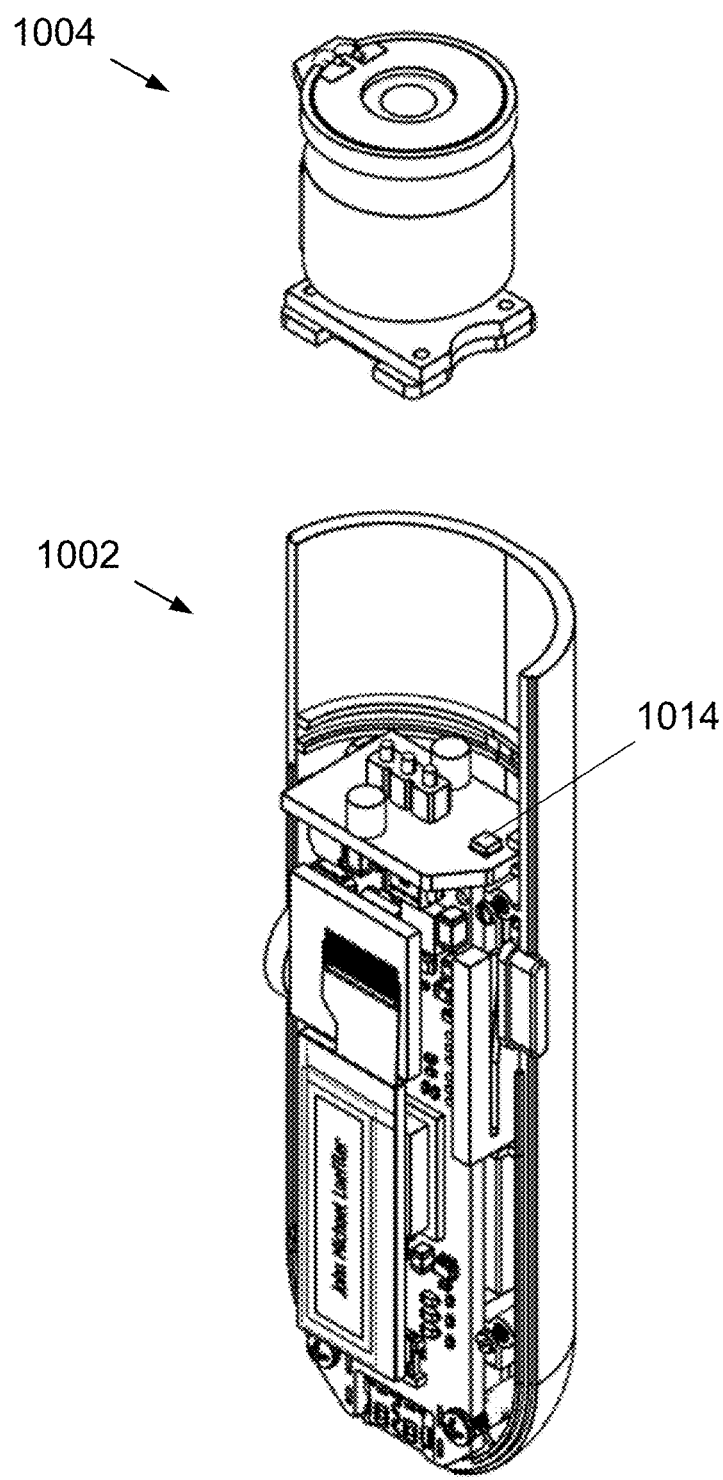

FIG. 14 is a view illustrating one or more components of the handheld base assembly 1002 and one or more components of the cartridge assembly 1004 of the electronic device 1000, wherein a pressure sensor 1014 of the handheld base assembly 1002 is perhaps best seen.

Figure 15:
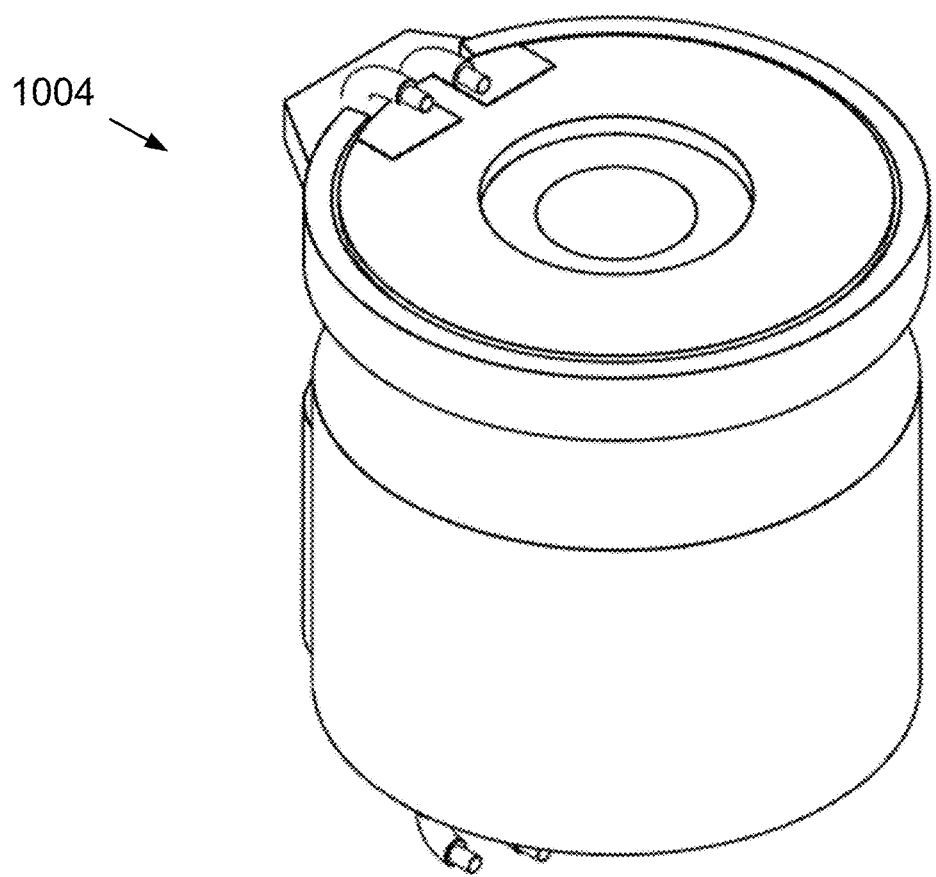

FIG. 15 is a view illustrating one or more components of the cartridge assembly 1004 of the electronic device 1000.

Figure 16:
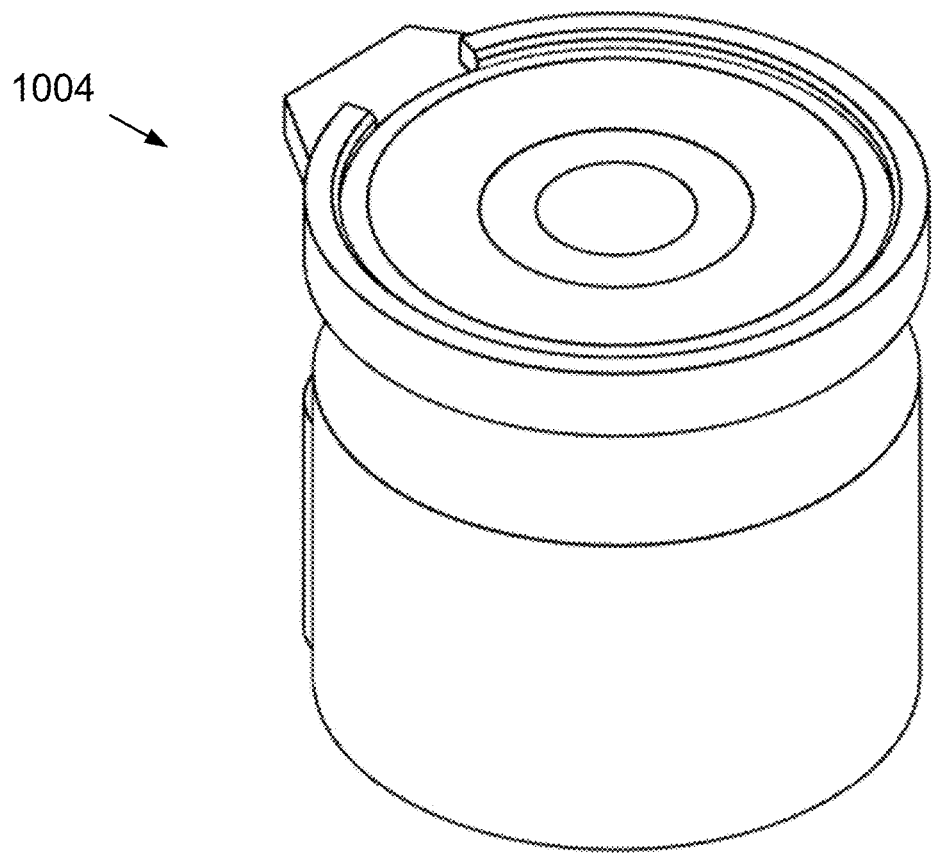

FIG. 16 is a view illustrating one or more components of the cartridge assembly 1004 of the electronic device 1000.

Figure 17:
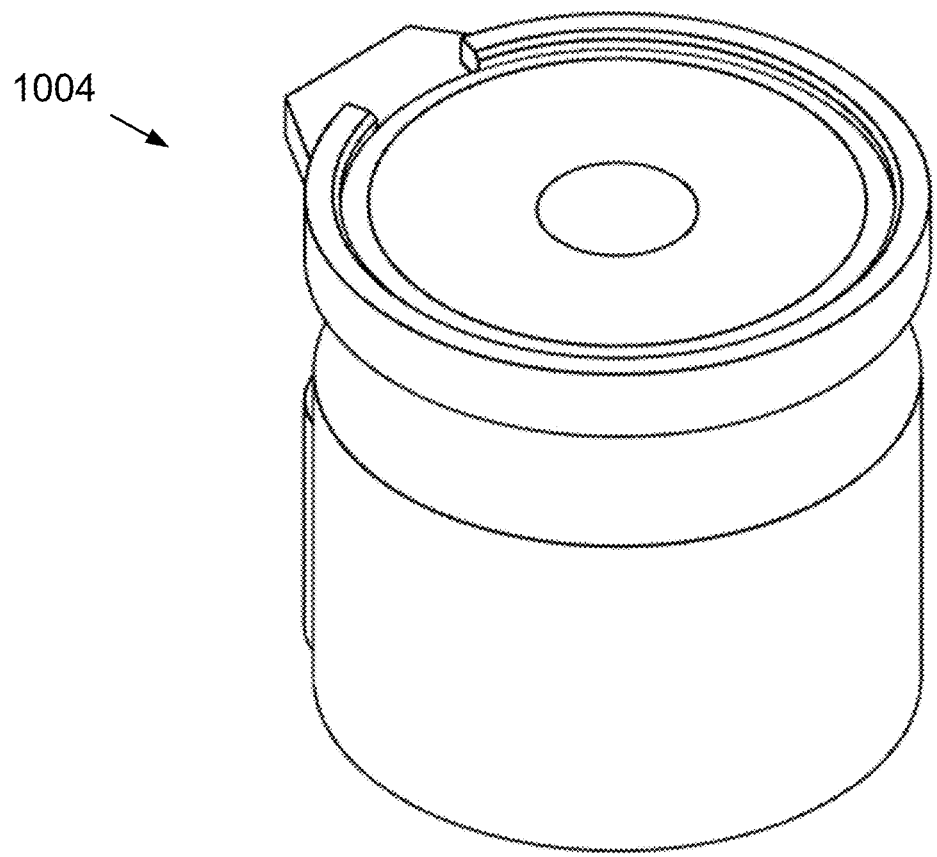

FIG. 17 is a view illustrating one or more components of the cartridge assembly 1004 of the electronic device 1000.

Figure 18:
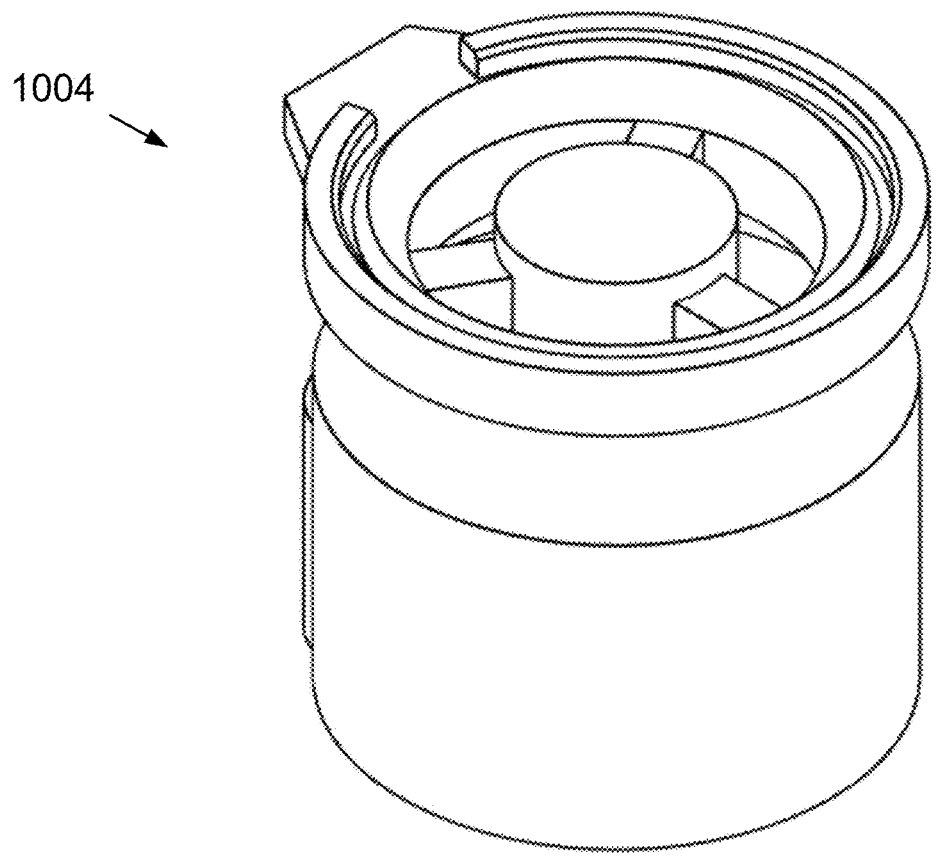

FIG. 18 is a view illustrating one or more components of the cartridge assembly 1004 of the electronic device 1000.

Figure 19:
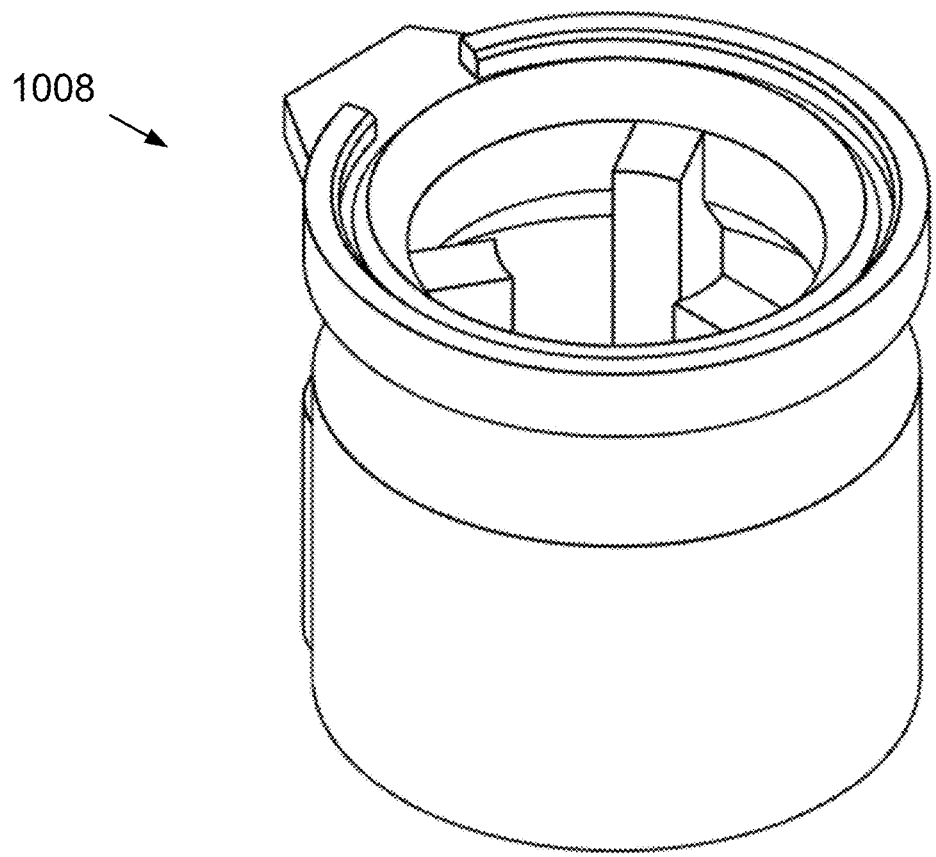

FIG. 19 is a view illustrating the bladder 1008 of the cartridge assembly 1004 of the electronic device 1000.

Figure 20:
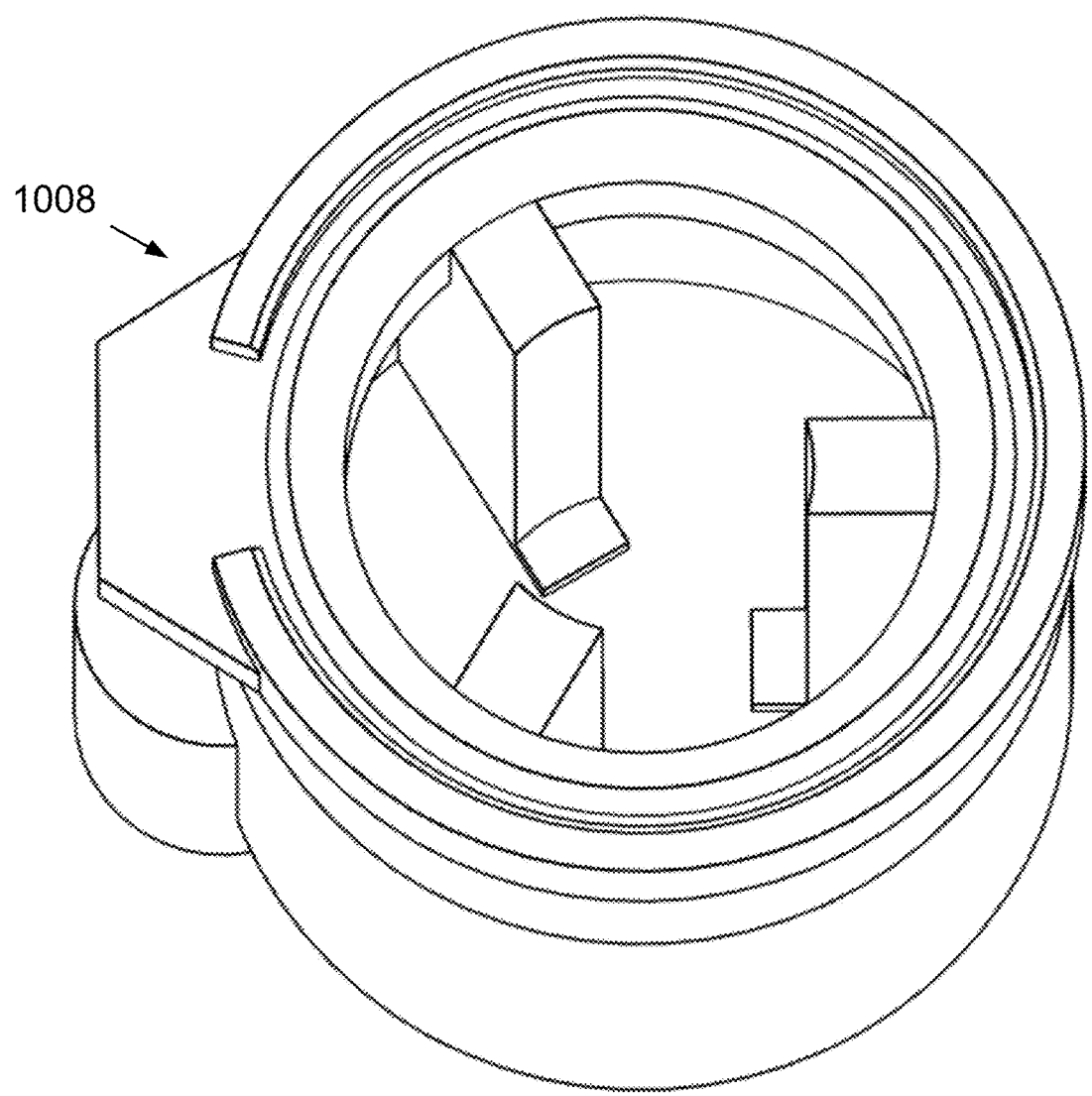

FIG. 20 is a view illustrating the bladder 1008 of the cartridge assembly 1004 of the electronic device 1000.

Figure 21:
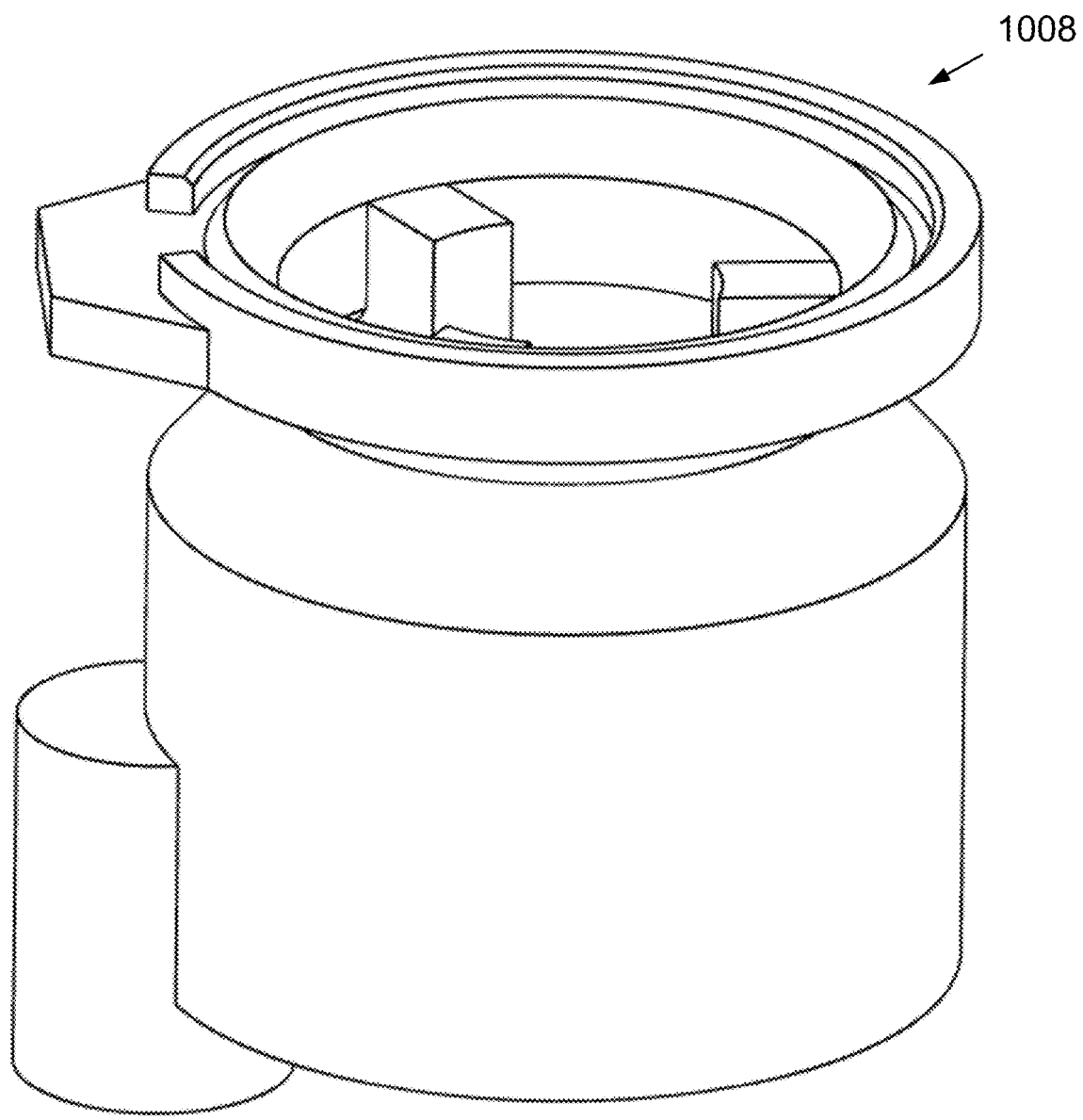

FIG. 21 is a view illustrating the bladder 1008 of the cartridge assembly 1004 of the electronic device 1000.

Figure 22:
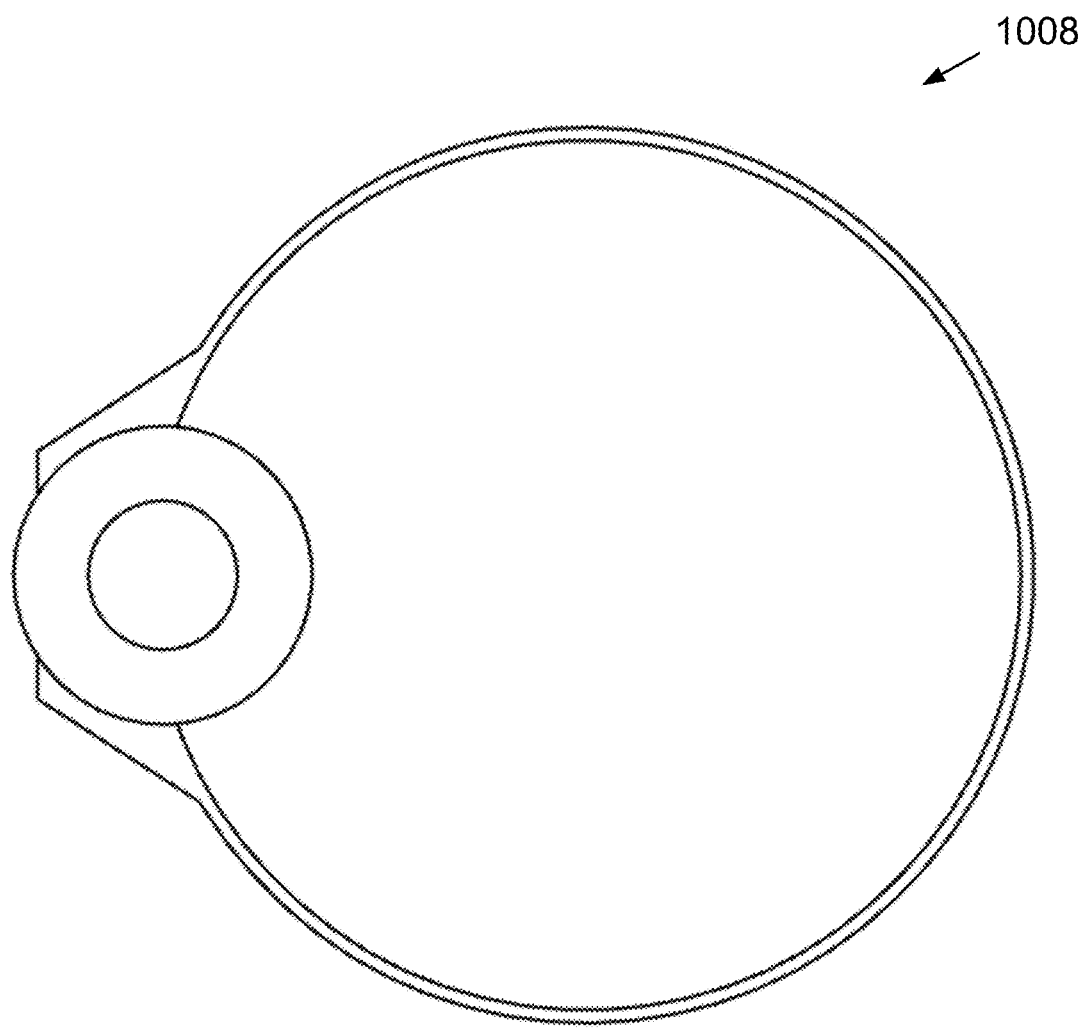

FIG. 22 is a view illustrating the bladder 1008 of the cartridge assembly 1004 of the electronic device 1000.

Figure 23:
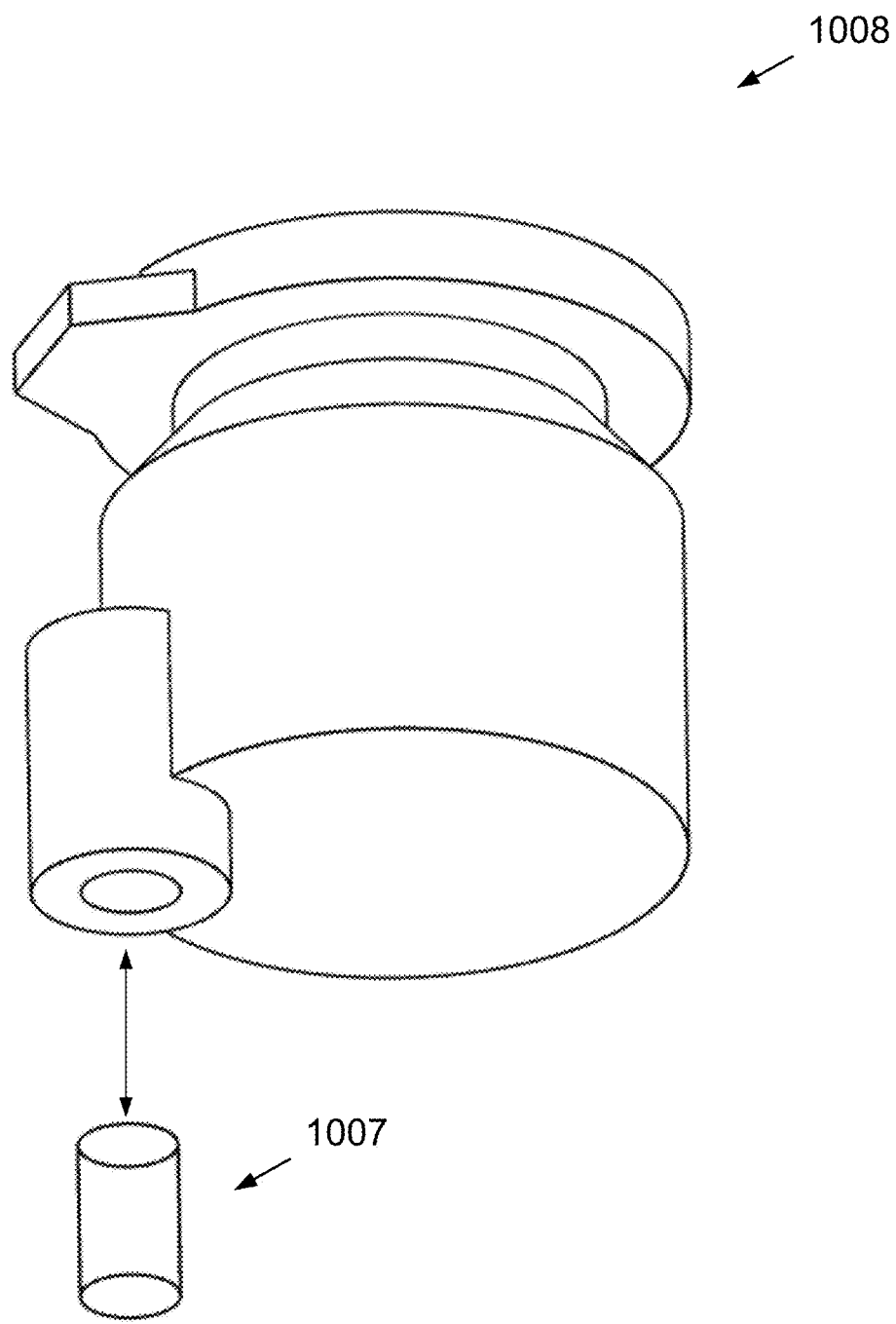

FIG. 23 is a view illustrating the bladder 1008 of the cartridge assembly 1004 of the electronic device 1000, wherein the plug 1007 of the bladder 1008 is shown removed from a fill port of the bladder.

Figure 24:
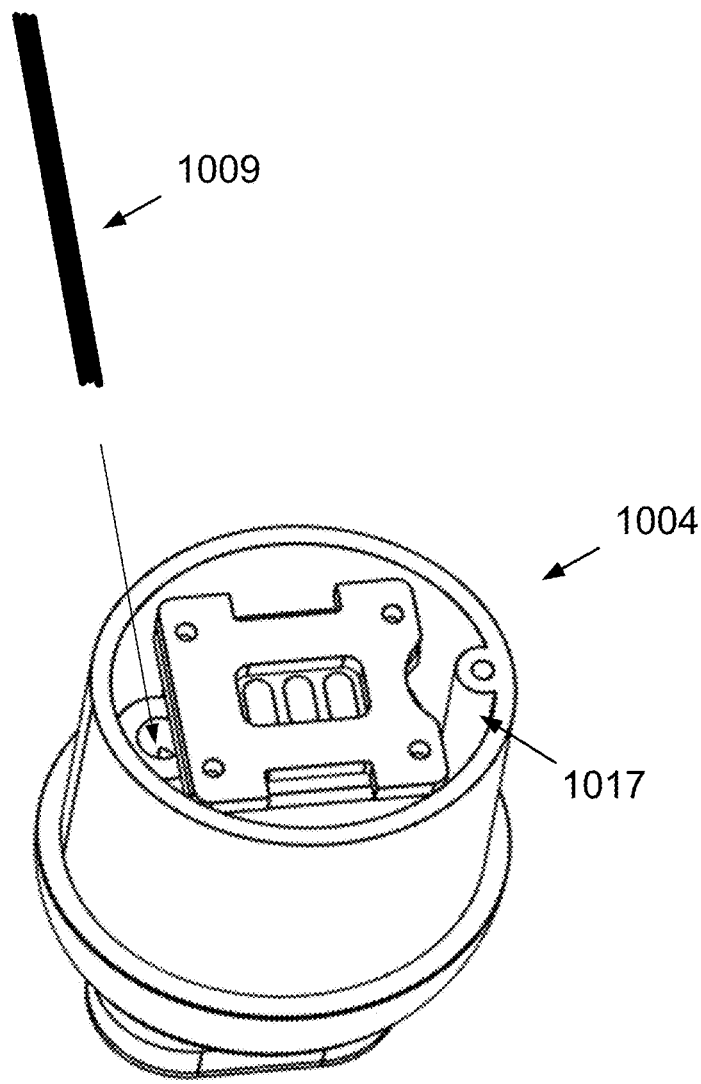

FIG. 24 illustrates a preferred method of making the cartridge assembly 1004 and, in particular, of filling the bladder of the cartridge assembly 1004 with a liquid to be aerosolized and inhaled, wherein an injection needle 1009 is inserted into the fill port of the bladder 1008 for filling of the bladder with the liquid.

Figure 25:
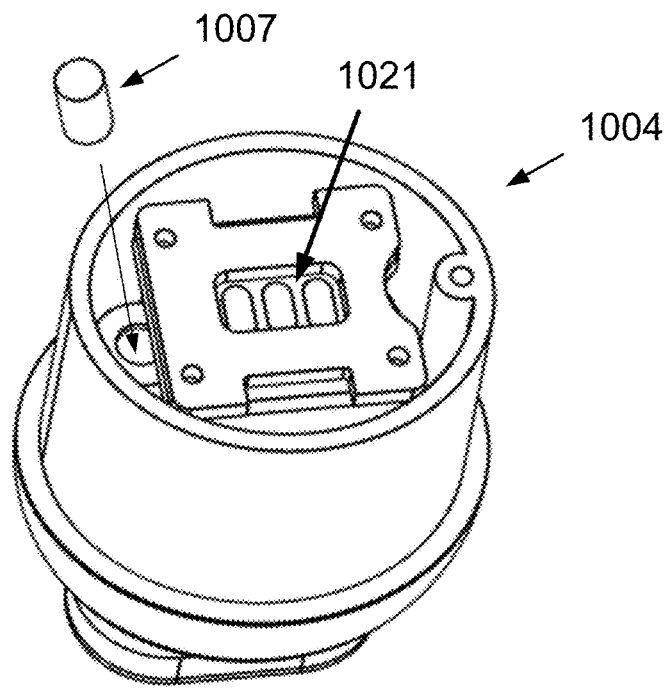

FIG. 25 illustrates the inserting of the plug 1007 into the fill port of the bladder for sealing of the bladder following the filling of the bladder with the liquid.

Figure 26:
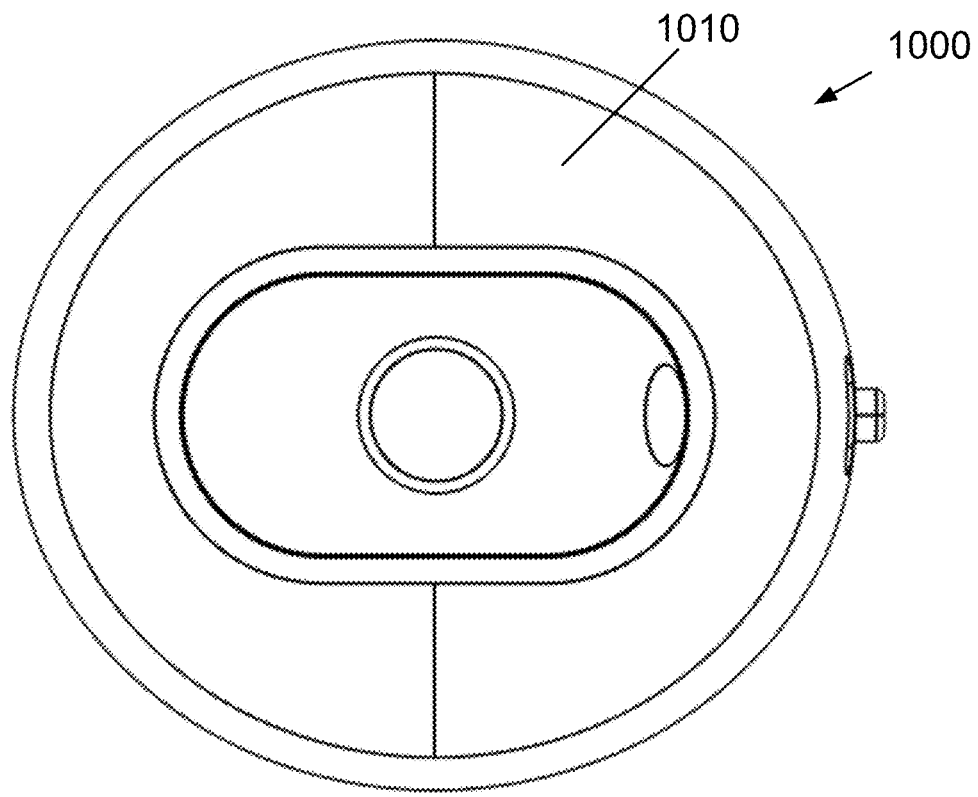

FIG. 26 is a top plan view of the electronic device 1000.

Figure 26A:
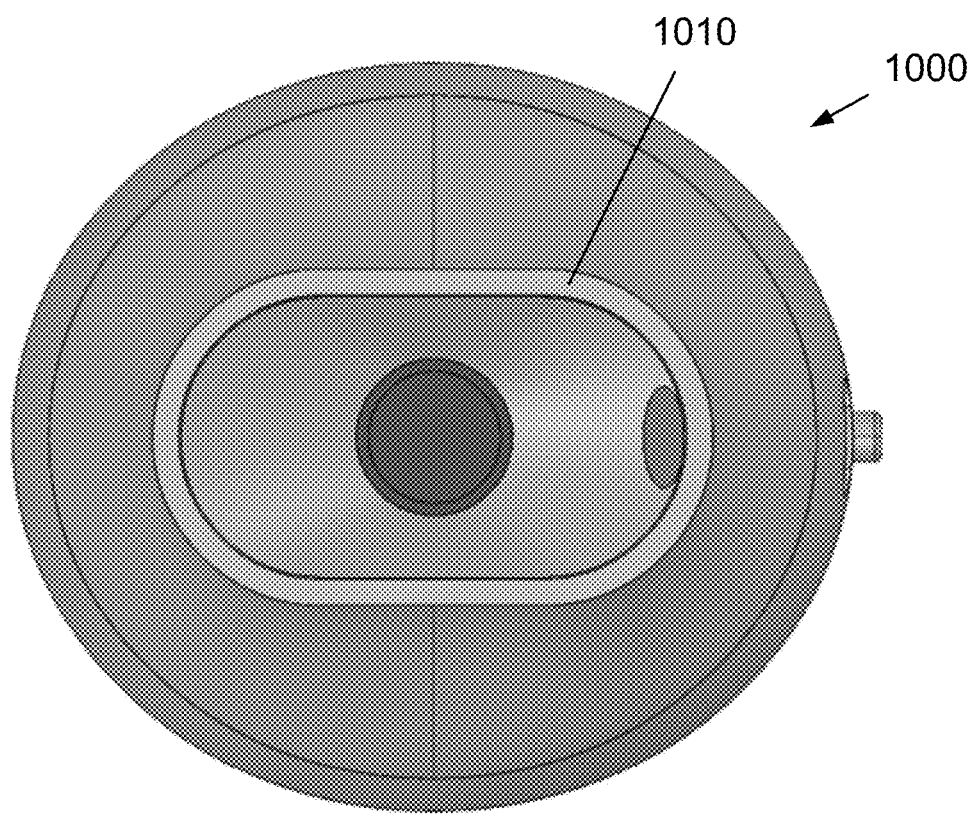

FIG. 26A is a shaded top plan view of the electronic device 1000.

Figure 26B:
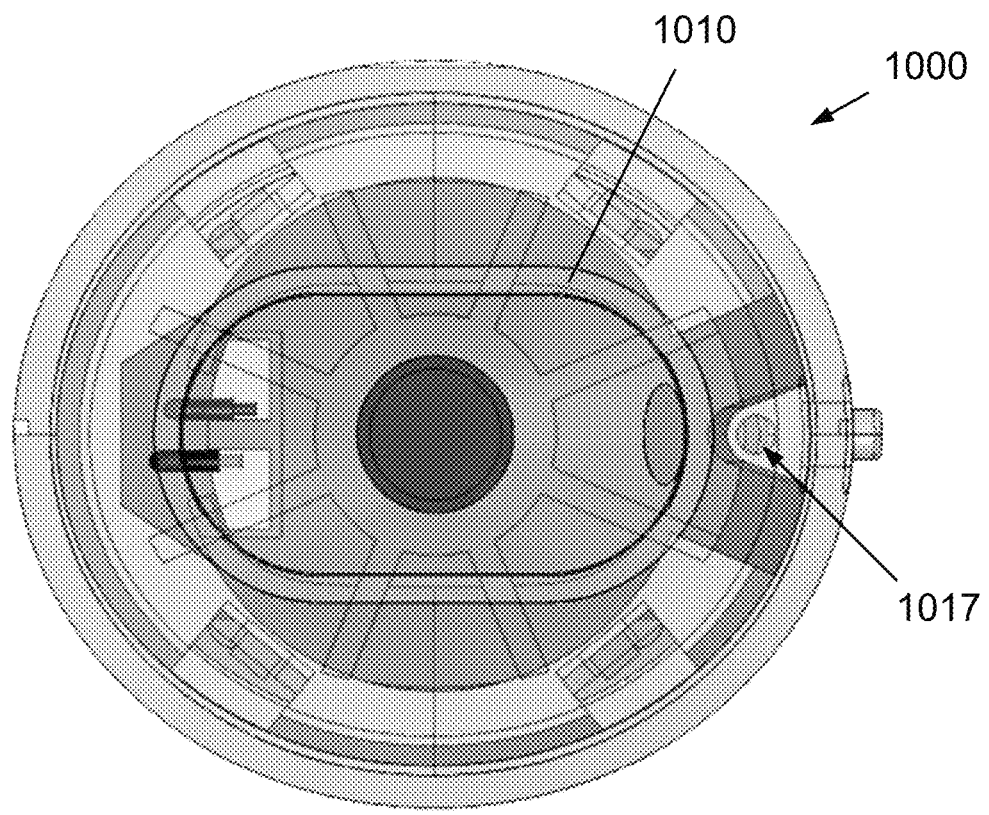

FIG. 26B is a shaded top plan view of the electronic device 1000, wherein a mouthpiece 1010 of the cartridge assembly 1004 is shown in transparent view.

FIG. 27 is the view of the electronic device 1000 of FIG. 26, wherein the mouthpiece 1010 is omitted.

FIG. 28 is a perspective view of the electronic device 1000 of FIG. 27, wherein the mouthpiece 1010 is omitted.

FIG. 29 is a perspective view of the electronic device 1000 of FIG. 27, wherein additional components are omitted and a lower body of the cartridge assembly 1004 is shown in transparent view for purposes of illustrated the diaphragm 1012 of the handheld base assembly 1002.

FIG. 30 is a top plan view of the mouthpiece 1010 of the cartridge assembly 1004.

FIG. 31 is a bottom plan view of the mouthpiece 1010 of the cartridge assembly 1004.

FIG. 32 is a bottom perspective view of the mouthpiece 1010 of the cartridge assembly 1004.

FIG. 33 discloses software flow for firmware of the electronic device 100,1000, which preferably is stored in memory and executed by a processor or microcontroller of the circuitry of the handheld base assembly 102,1002.

FIGS. 34-44 illustrates various user interface screens 110,111,112,113,114,115 for apps that are installed and run on smartphones, such as an iPhone or an Android device, and which apps communicate with the electronic devices wirelessly using a communications protocol such as Bluetooth or Wi-Fi.

FIG. 45 illustrates possible user experiences when interacting with graphical user interfaces ("GUIs") of the software in accordance with one or more aspects and features of the invention, which GUIs and sequences thereof are intended to drive adherence and compliance with prescribed medication use.

FIG. 46 illustrates features and capabilities of the software in accordance with one or more aspects and features of the invention, whether performed on the electronic device or on a mobile application on a smartphone, tablet device, or personal computer that is in communication with the electronic device.

FIG. 47 illustrates an exemplary instructions-for-use document (IFU) that is preferably included with commercial packaging represented in the schematic illustration of FIG. 1.

DETAILED DESCRIPTION

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

With regard solely to construction of any claim with respect to the United States, no claim element is to be interpreted under 35 U.S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once but not necessarily every time during performance of the claimed method.

Furthermore, it is important to note that, as used herein, "comprising" is open-ended insofar as that which follows such term is not exclusive. Additionally, "a" and "an" each generally denotes "at least one" but does not exclude a plurality unless the contextual use dictates otherwise. Thus, reference to "a picnic basket having an apple" is the same as "a picnic basket comprising an apple" and "a picnic basket including an apple", each of which identically describes "a picnic basket having at least one apple" as well as "a picnic basket having apples"; the picnic basket further may contain one or more other items beside an apple. In contrast, reference to "a picnic basket having a single apple" describes "a picnic basket having only one apple"; the picnic basket further may contain one or more other items beside an apple. In contrast, "a picnic basket consisting of an apple" has only a single item contained therein, i.e., one apple; the picnic basket contains no other item.

When used herein to join a list of items, "or" denotes "at least one of the items" but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers"; the picnic basket further may contain one or more other items beside cheese and crackers.

When used herein to join a list of items, "and" denotes "all of the items of the list". Thus, reference to "a picnic basket having cheese and crackers" describes "a picnic basket having cheese, wherein the picnic basket further has crackers", as well as describes "a picnic basket having crackers, wherein the picnic basket further has cheese"; the picnic basket further may contain one or more other items beside cheese and crackers.

The phrase "at least one" followed by a list of items joined by "and" denotes an item of the list but does not require every item of the list. Thus, "at least one of an apple and an orange" encompasses the following mutually exclusive scenarios: there is an apple but no orange; there is an orange but no apple; and there is both an apple and an orange. In these scenarios if there is an apple, there may be more than one apple, and if there is an orange, there may be more than one orange. Moreover, the phrase "one or more" followed by a list of items joined by "and" is the equivalent of "at least one" followed by the list of items joined by "and".

Referring now to the drawings, one or more preferred embodiments of the invention are next described. The following description of one or more preferred embodiments is merely exemplary in nature and is in no way intended to limit the invention, its implementations, or uses.

Figure 1:
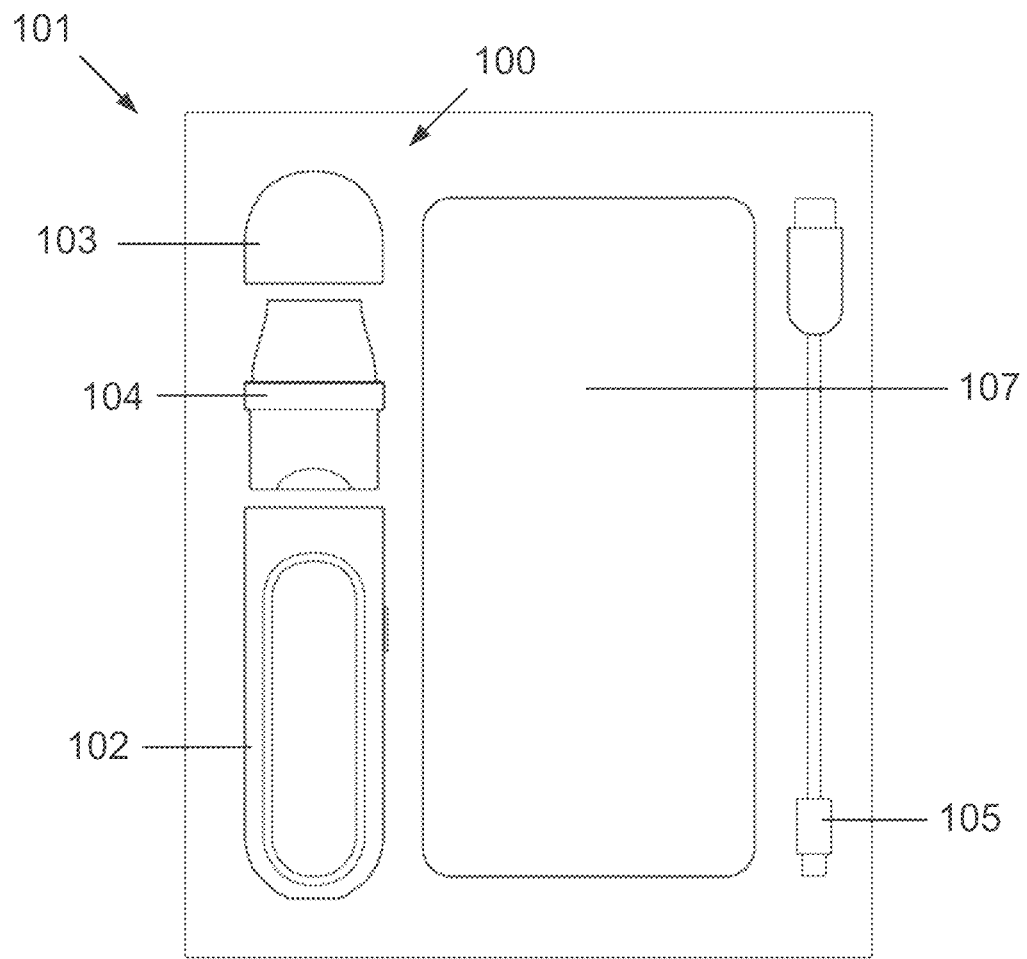
Figure 47:
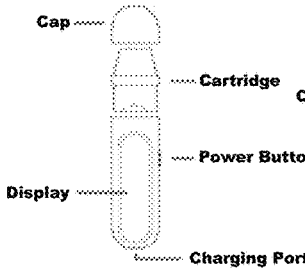

In particular, FIG. 1 is a schematic illustration of commercial packaging comprising a container 101 containing an electronic device 100 for producing an aerosol for inhalation by a person in accordance with one or more aspects and features of the invention, wherein a handheld base assembly 102 and a cartridge assembly 104 of the electronic device 100 are shown as separated, individual components together with a cap 103, USB charging cord 105, and instructions for use or "IFU" 107. The preferred IFU 107 are illustrated in FIG. 47.

Figure 2:
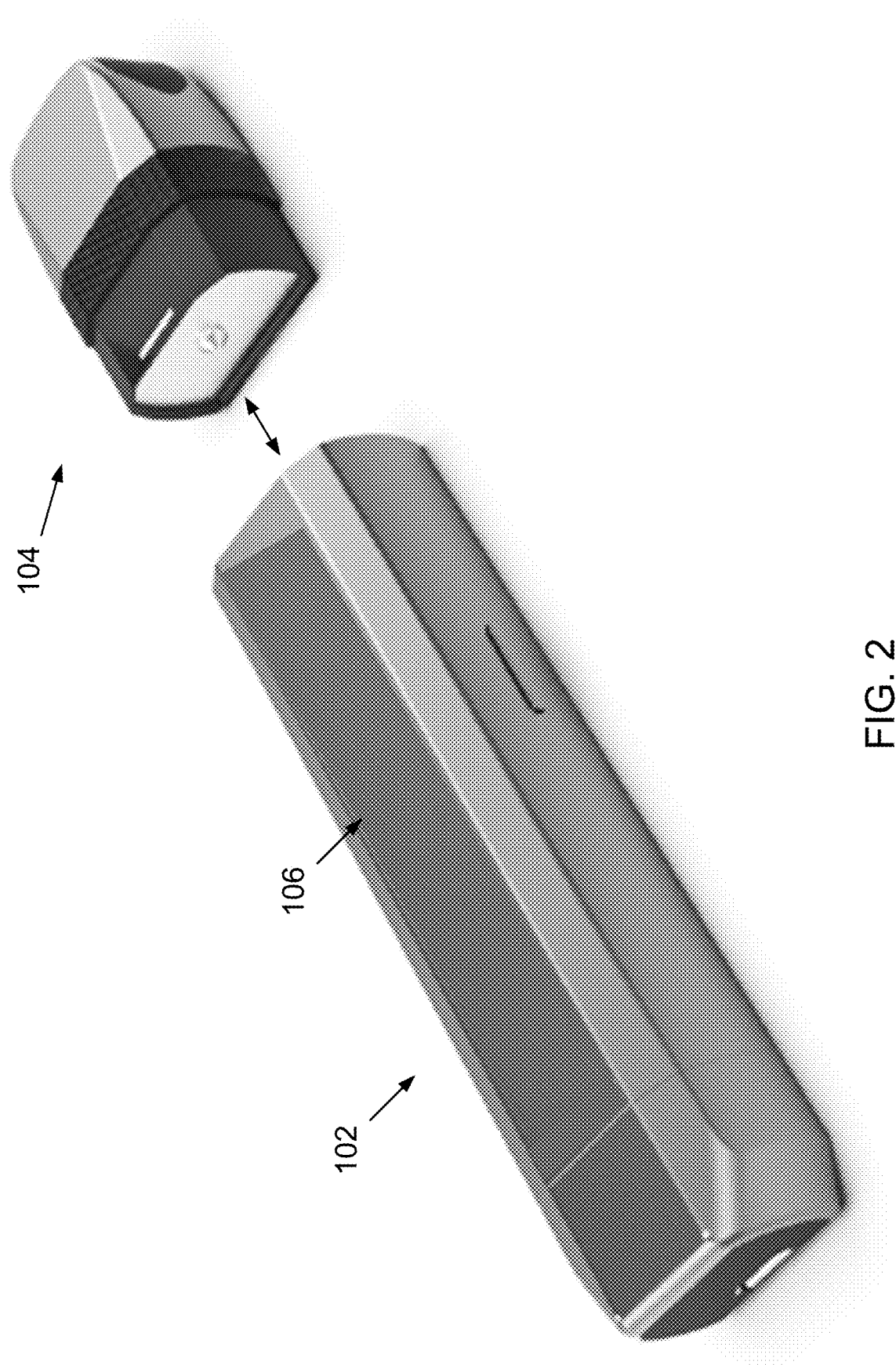

FIG. 2 illustrates a perspective view of the preferred electronic device 100 of FIG. 1 and indicates the removable coupling together of the handheld base assembly 102 and the cartridge assembly 104.

Figure 3:
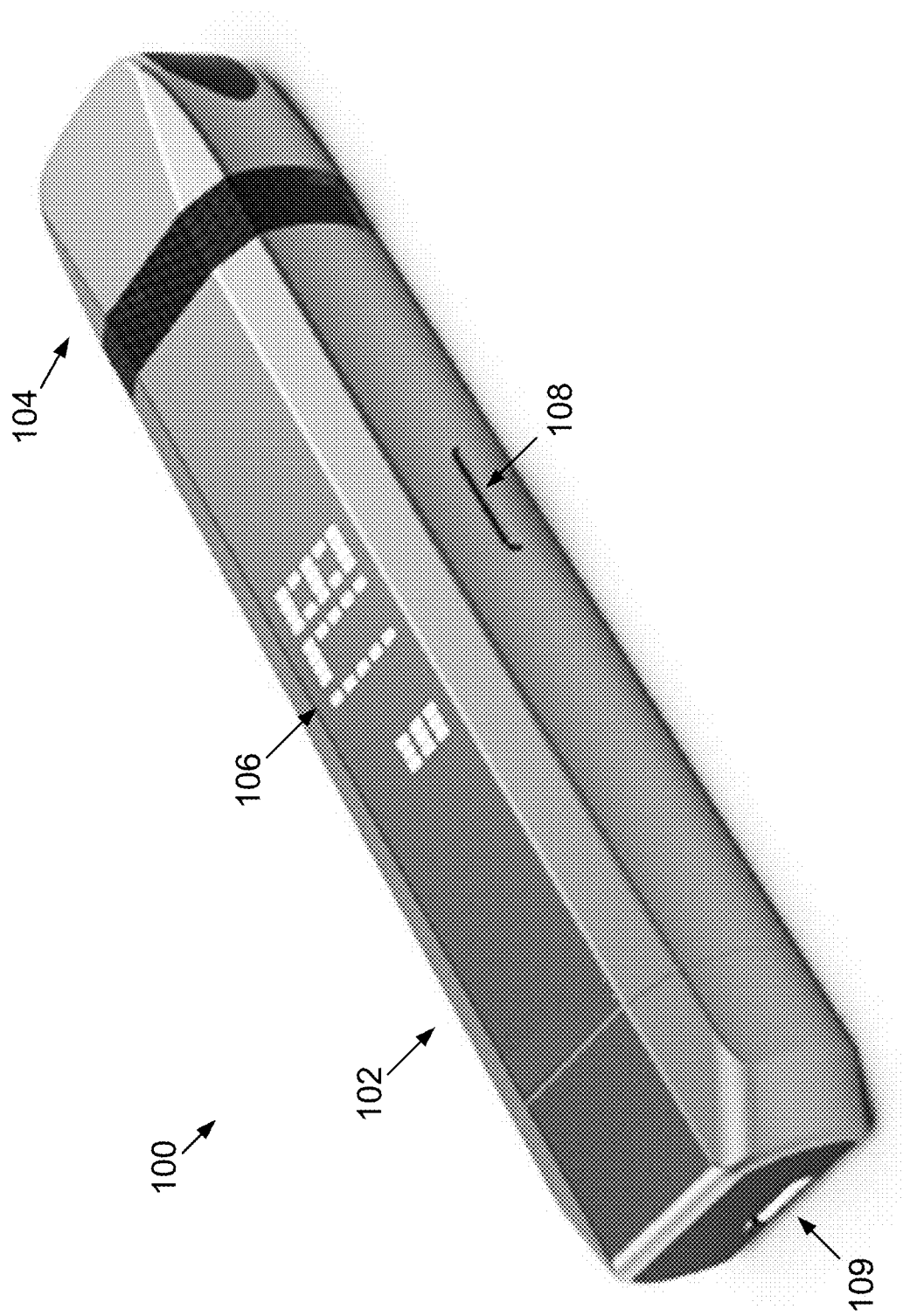
Figure 6:
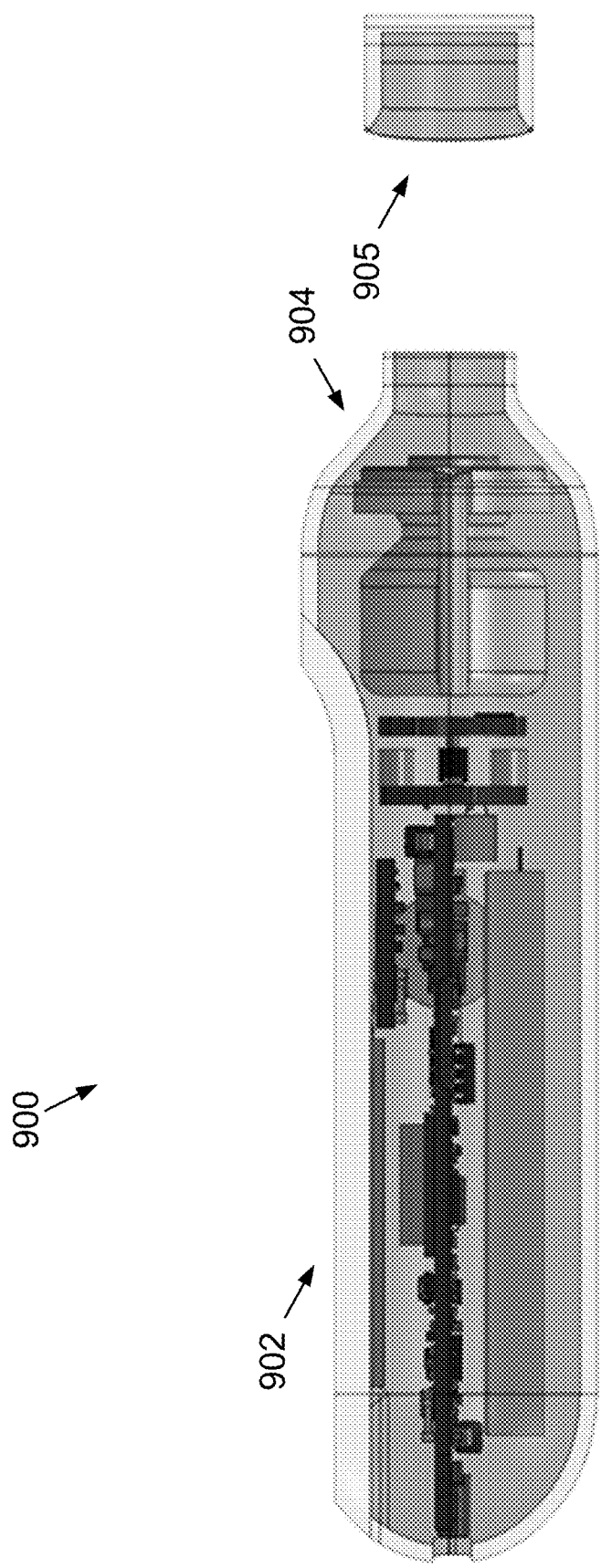
Figure 7:
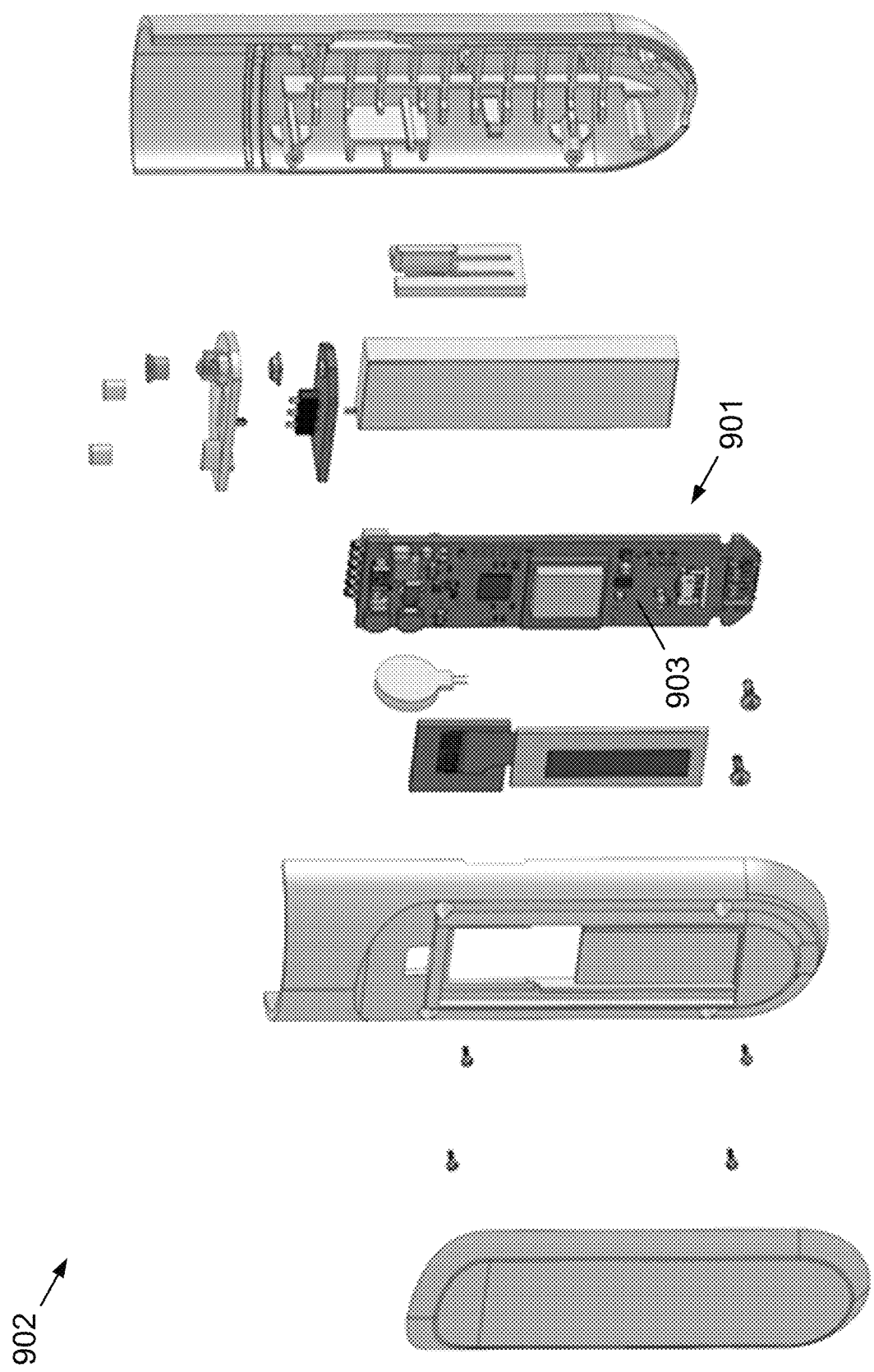
Figure 8:
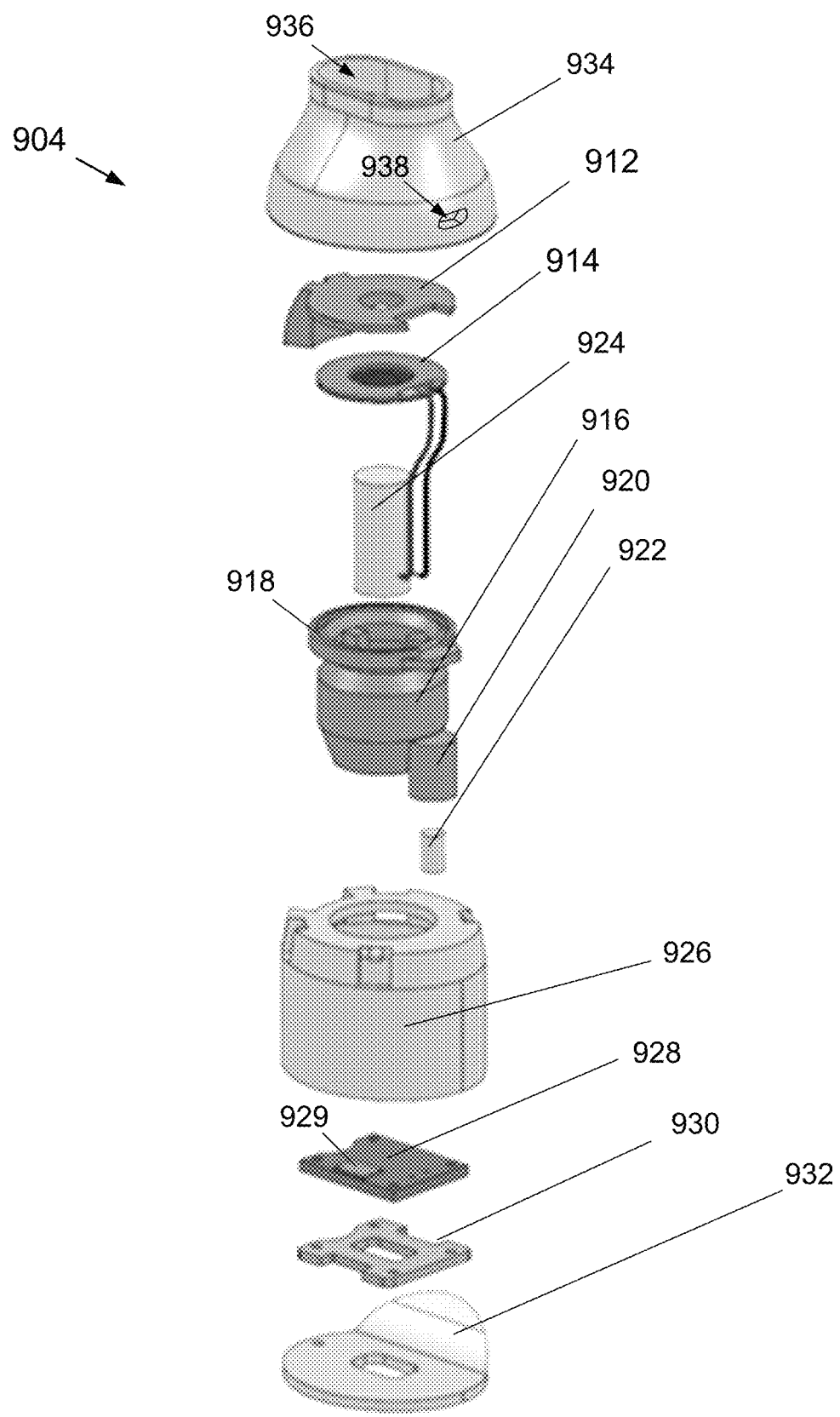

FIG. 3 illustrates a perspective view of the electronic device 100 when the handheld base assembly 102 and the cartridge assembly 104 are removably coupled together.

As shown in FIG. 3, "178" doses are indicated on a display 106 of the electronic device 100. The number of doses preferably indicates how many doses have been metered by the device from a reservoir of the cartridge assembly 104, or possibly one like it. Alternatively, number of doses represents the number remaining to be provided by the electronic device with the current cartridge assembly coupled thereto.

Specifically, when the handheld base assembly 102 and the cartridge assembly 104 are coupled together, firmware in memory of the handheld base assembly 102 and executed by a processor or microcontroller of the circuitry of the handheld base assembly 102 reads from a nonvolatile memory of the cartridge assembly 104 a number of doses that have been dispensed from the reservoir of the cartridge assembly 104, whether using the handheld base assembly 102 or using another handheld base assembly of another electronic device of the invention.

Optionally, the handheld base assembly 102 and the cartridge assembly 104 can be paired such that the cartridge assembly 104 only works with the handheld base assembly 102 by storing a unique identifier or other authenticating information in the cartridge assembly 104 by which the firmware of the handheld base assembly is configured to authenticate the cartridge assembly 102. Such authenticating information preferably is permanently stored in read-only memory of the cartridge assembly 104. Such pairing can be performed at time of manufacture, or when a new cartridge assembly 104 is first used with a handheld base assembly 102. Alternatively, such authenticating information can be communicated to the handheld base assembly wirelessly over the Internet once the cartridge assembly to be used with the handheld base assembly 102 is known, such as when a specific cartridge may be prescribed or a prescription filled using the specific cartridge assembly. In this respect, the circuitry of the handheld base assembly 102 preferably includes a transceiver for wireless communications, including via Bluetooth, Wi-Fi, or other wireless communications protocol.

The display 106 further preferably shows a battery level of the electronic device 100. As shown in FIG. 3, the battery level is nine units. The battery preferably is rechargeable using, for example, a USB port as seen at 109. The display may be an organic light-emitting diode ("OLED") or light-emitting diode "(LCD") screen.

The display preferably turns off after a predetermined period of time to avoid draining the battery. The display is turned on by positioning the handheld base assembly 102 to an orientation for reading of the display, by pushing and releasing a button 108, or by some other user input mechanism. The button 108 also preferably initiates a dosing by, for example, a depressing the button 108 for a prolonged period of time (relative to a quick pressing to illuminate the display).

Alternatively, the button 108 is used to wake the electronic device 100 (including display for a predetermined period of time), and a pressure sensor of the handheld base assembly 102 detects when a breath is drawn from a mouthpiece of the cartridge assembly 104 for causing the aerosolization of a metered dose. In this respect, when the pressure sensor detects a breath, the haptic engine is activated to provide sensory feedback to the user that a breath has been detected and that a dose is being/will be aerosolized. The magnitude of the vibrations caused by the haptic engine and length of activation preferably are settings that can be adjusted by a user through an app. The haptic vibration also may be used to signal the end of a precisely metered dose.

FIG. 4 illustrates a perspective view of another electronic device 900 for producing an aerosol for inhalation by a person in accordance with one or more aspects and features of the invention, wherein when a handheld base assembly 902 and a cartridge assembly 904 with a sealing cap 905 are removably coupled together.

FIG. 5 is another view of the electronic device 900 with the sealing cap 905 removed to expose an opening of a mouthpiece of the cartridge assembly 904.

FIG. 6 is a side elevational view in partial transparency of the electronic device 900.

FIG. 7 is an exploded view of the handheld base assembly 902 of the electronic device 900. As shown in FIG. 7, the handheld base assembly 902 comprises circuitry 901 in the form of a printed circuit board 903 which includes a processor or microcontroller and memory.

FIG. 8 is an exploded view of the cartridge assembly 904 of the electronic device 900. The cartridge assembly 904 comprises a pressure ring 912; a mesh assembly 914; and a liquid reservoir in the form of a bladder 916. The mesh assembly 914 comprises a piezo transducer disc or annulus, perforated mesh centrally located and supported by the piezo, and electrical wires for actuating the piezo and effecting oscillation of the mesh. The bladder 916 comprises a rim 918 configured to receive and effect a seal with the mesh assembly 914. The mesh preferably comprises perforated 316L stainless steel. The mesh assembly is located between the pressure ring 912 and the bladder 916. The bladder 916 includes a fill port 920 and plug 922 for sealing the fill port 922, whereby the bladder 916 may be filled with a liquid from underneath. The bladder 916 preferably has a capacity of 1.5 ml. A wick 924 is located within the bladder 916 that facilitates conveyance of liquid to the mesh. The bladder 916 is contained within a cartridge housing or body 926. A printed circuit board 928 with non-transitory computer-readable medium, e.g., flash memory 929, and a plate 930 for securement with magnets of the handheld base assembly, also are shown to be contained within the cartridge body 926. A bottom cap 932 covers the bottom of the cartridge body 926. An opening in the bottom cap 923 and a corresponding opening in the plate 930 in register with the opening in the bottom cap 923 facilitate passage therethrough of one or more pins of the handheld base assembly to the printed circuit board 928, by which the cartridge assembly is connected with the handheld base assembly for electronic communication and for providing power to and driving the oscillations of the mesh assembly 914. A mouthpiece 934 attaches to a top of the cartridge body 926 in covering relation to the pressure ring 912 and mesh assembly 914. The mouthpiece 934 defines an interior area located over the pressure ring from which the aerosolized liquid is suctioned, and a mouth opening 936 through which the aerosolized liquid is suctioned into the mouth of a user. The interior area is vented by port 938 for facilitating airflow through the interior area and out the mouth opening 936 when a breath is dawn. The pressure ring preferably is a distinct silicone rubber component that applies even and consistent circumferential pressure to the mesh assembly. It is designed in a manner to not dampen the functionality and oscillation potential of the vibrating mesh. The bladder preferably is made from silicone and is a compliant component that interfaces with the mesh assembly to simultaneously provide a liquid tight seal while also supporting the piezo for optimal vibration characteristics, thus not dampening or muting the perforated mesh from creating an aerosol. The pressure ring along with the bladder work in concert with optimal driving parameters of the firmware to create an orientation agnostic vibrating mesh nebulizer.

The vibrating mesh nebulizer stack of the electronic device 900 is designed with a fully sealed airpath that is compliant with medical airpath ISO 18625 and medical device ISO 10993 standards, each standard of which is incorporated herein by reference as of Apr. 22, 2022. In particular, the electronic device and, specifically, the cartridge assembly and handheld base assembly, preferably collectively define an enclosed interior air passageway leading from the interior area within the mouthpiece from which the aerosolized liquid is suctioned to an arrangement in the handheld base assembly that includes a pressure sensor by which a breath drawn on the mouthpiece is detected. The cartridge body of the cartridge assembly preferably defines the air passageway leading from the interior space of the mouthpiece to an opening on the bottom of the cartridge body, and the handheld base assembly preferably comprises a sealing component and protuberance. The sealing component preferably engages the area around the opening on the bottom of the cartridge body so as to seal the opening when the cartridge body is coupled to the handheld base assembly. The protuberance preferably defines an air passageway from the opening in the cartridge body to a diaphragm, which closes of the air passageway. Air within the passageway is thereby trapped, and a decrease in pressure within the interior area of the mouthpiece due to the drawing of a breath results in a decrease in pressure in the air passageway of the protuberance at the diaphragm, which in turn causes the diaphragm to move outwardly into or toward an interior of the air passageway. The diaphragm is located next to and in fluid communication with a pressure sensor and is configured to trigger the pressure sensor when the diaphragm so moves due to the drop in pressure in the air passageway of the protuberance. Preferably, all components (or portions thereof) defining the enclosed air passageway are made from medical grade materials in compliance with ISO 18562 and ISO 10993.

The cartridge assembly is designed to be disposable, whereas the handheld base assembly is designed to be reusable. Additionally, the electronic device preferably is Bluetooth® enabled, features breath-actuation of a measured dosage, and is orientation-agnostic in operation. The Bluetooth capabilities enable user interaction via a smartphone, table, or personal computer with an app for use with the electronic device. User interfaces of the app preferably facilitate use of the handheld base assembly with multiple different cartridge assemblies, which GUIs are described below.

Figure 9:
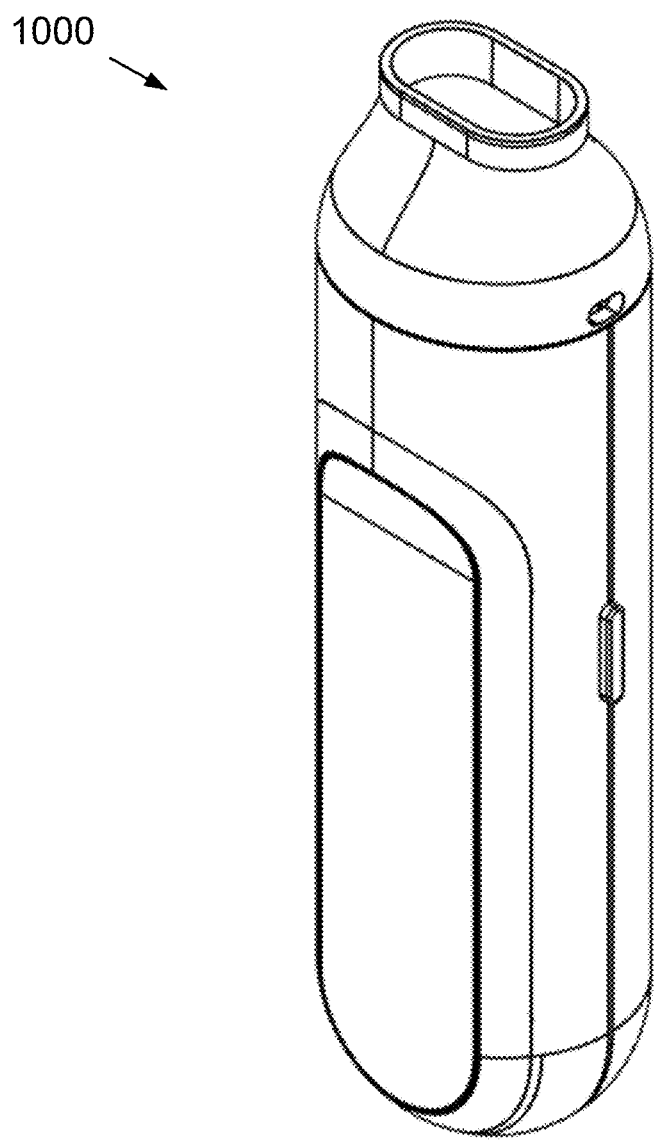
FIG. 9 is a perspective view of another electronic device 1000 for producing an aerosol for inhalation by a person in accordance with one or more aspects and features of the invention.

FIG. 9 is a perspective view of another electronic device 1000 for producing an aerosol for inhalation by a person in accordance with one or more aspects and features of the invention.

Figure 10:
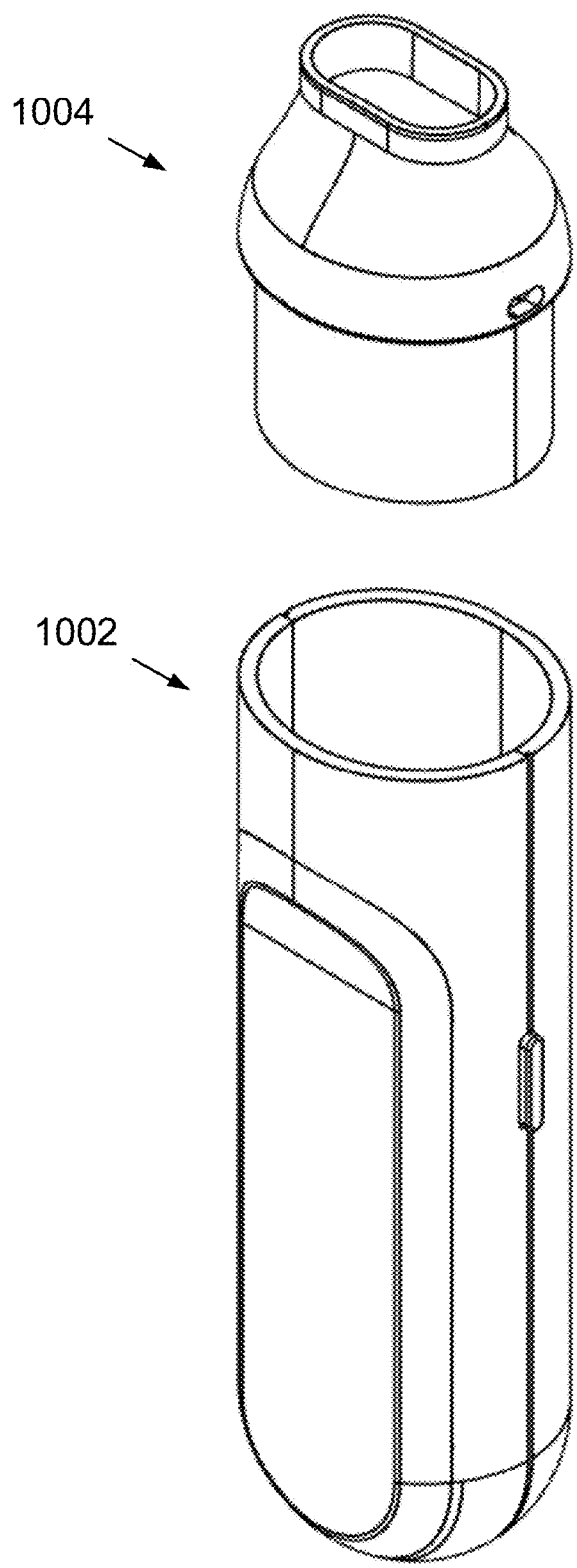
FIG. 10 is a view illustrating the uncoupling of the handheld base assembly 1002 and the cartridge assembly 1004 of the electronic device 1000.

FIG. 10 is a view illustrating the uncoupling of the handheld base assembly 1002 and the cartridge assembly 1004 of the electronic device 1000.

Figure 11:
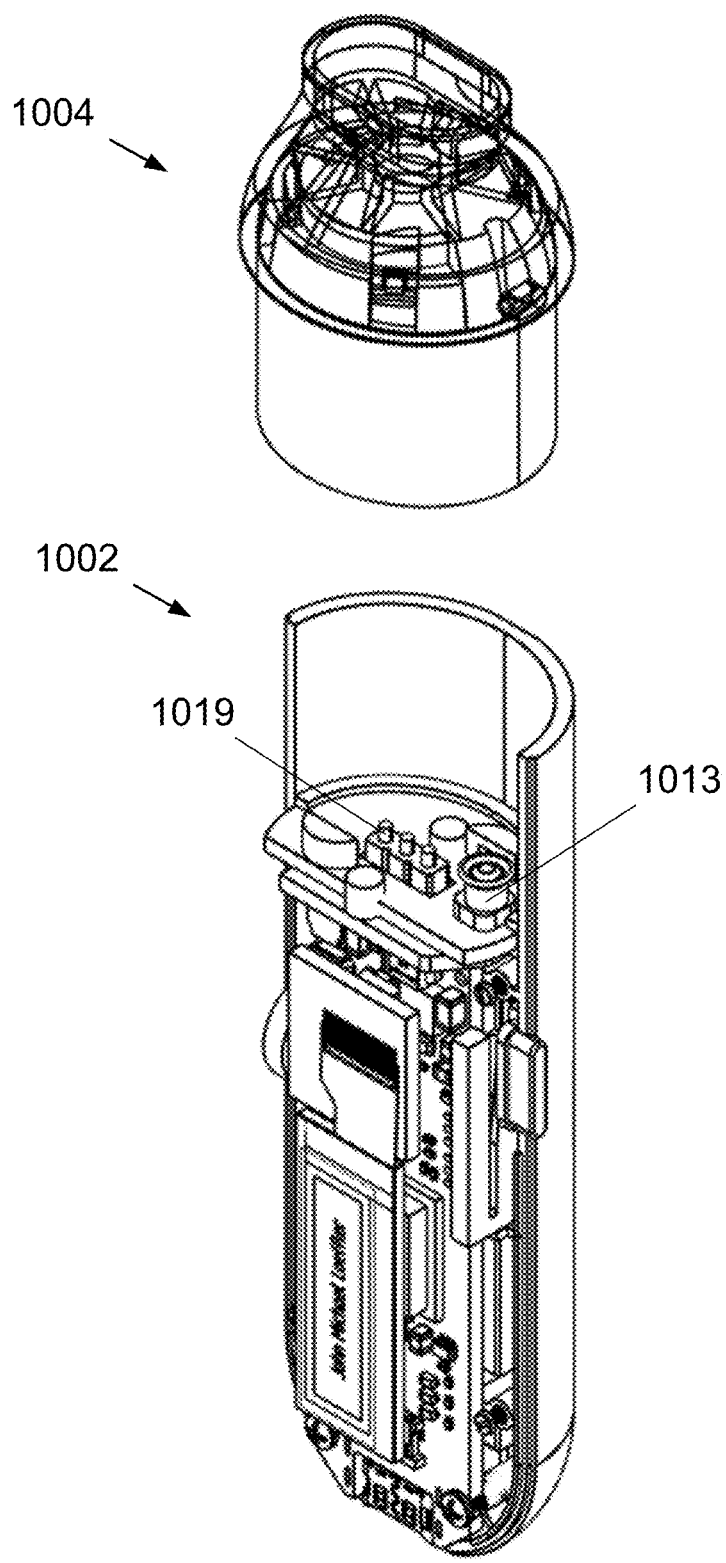
FIG. 11 is a view illustrating one or more components of the handheld base assembly 1002 and one or more components of the cartridge assembly 1004 of the electronic device 1000, wherein a sealing component 1013 is perhaps best seen.

FIG. 11 is a view illustrating one or more components of the handheld base assembly 1002 and one or more components of the cartridge assembly 1004 of the electronic device 1000, wherein a sealing component 1013 is perhaps best seen. As discussed above, the sealing component 1013 creates an airtight seal with the cartridge body around an opening therein when the cartridge assembly is coupled with the handheld base assembly. The opening is to the airflow passageway leading from the interior area of the mouthpiece; the airflow passageway is perhaps best shown in FIG. 13, wherein a channel 1017 in the cartridge body defines this air passageway. FIG. 11 also perhaps best shows pins 1019 by which the handheld base assembly is connected with the cartridge assembly for communication therewith and for providing power to and driving the oscillations of the piezo. The corresponding contacts 1021 for these pins are perhaps best shown in FIG. 25.

FIG. 12 is a view illustrating one or more components of the handheld base assembly 1002 and one or more components of the cartridge assembly 1004 of the electronic device 1000, wherein a protuberance 1011 defined by a wall of the handheld base assembly 1002 is seen, the protuberance defining in part the enclosed air passageway to a diaphragm 1012 of the handheld base assembly 1002 (perhaps best seen in FIG. 13).

FIG. 13 is a view illustrating one or more components of the handheld base assembly 1002 and one or more components of the cartridge assembly 1004 of the electronic device 1000, wherein the diaphragm 1012 is perhaps best seen.

FIG. 14 is a view illustrating one or more components of the handheld base assembly 1002 and one or more components of the cartridge assembly 1004 of the electronic device 1000, wherein a pressure sensor 1014 of the handheld base assembly 1002 is perhaps best seen.

FIG. 15 is a view illustrating one or more components of the cartridge assembly 1004 of the electronic device 1000.

FIG. 16 is a view illustrating one or more components of the cartridge assembly 1004 of the electronic device 1000.

FIG. 17 is a view illustrating one or more components of the cartridge assembly 1004 of the electronic device 1000.

FIG. 18 is a view illustrating one or more components of the cartridge assembly 1004 of the electronic device 1000.

FIG. 19 is a view illustrating the bladder 1008 of the cartridge assembly 1004 of the electronic device 1000.

FIG. 20 is a view illustrating the bladder 1008 of the cartridge assembly 1004 of the electronic device 1000.

FIG. 21 is a view illustrating the bladder 1008 of the cartridge assembly 1004 of the electronic device 1000.

FIG. 22 is a view illustrating the bladder 1008 of the cartridge assembly 1004 of the electronic device 1000.

FIG. 23 is a view illustrating the bladder 1008 of the cartridge assembly 1004 of the electronic device 1000, wherein the plug 1007 of the bladder 1008 is shown removed from a fill port of the bladder.

FIG. 24 illustrates a preferred method of making the cartridge assembly 1004 and, in particular, of filling the bladder of the cartridge assembly 1004 with a liquid to be aerosolized and inhaled, wherein an injection needle 1009 is inserted into the fill port of the bladder 1008 for filling of the bladder with the liquid.

FIG. 25 illustrates the inserting of the plug 1007 into the fill port of the bladder for sealing of the bladder following the filling of the bladder with the liquid.

FIG. 26 is a top plan view of the electronic device 1000.

FIG. 26A is a shaded top plan view of the electronic device 1000.

FIG. 26B is a shaded top plan view of the electronic device 1000, wherein a mouthpiece 1010 of the cartridge assembly 1004 is shown in transparent view.

Figure 27:
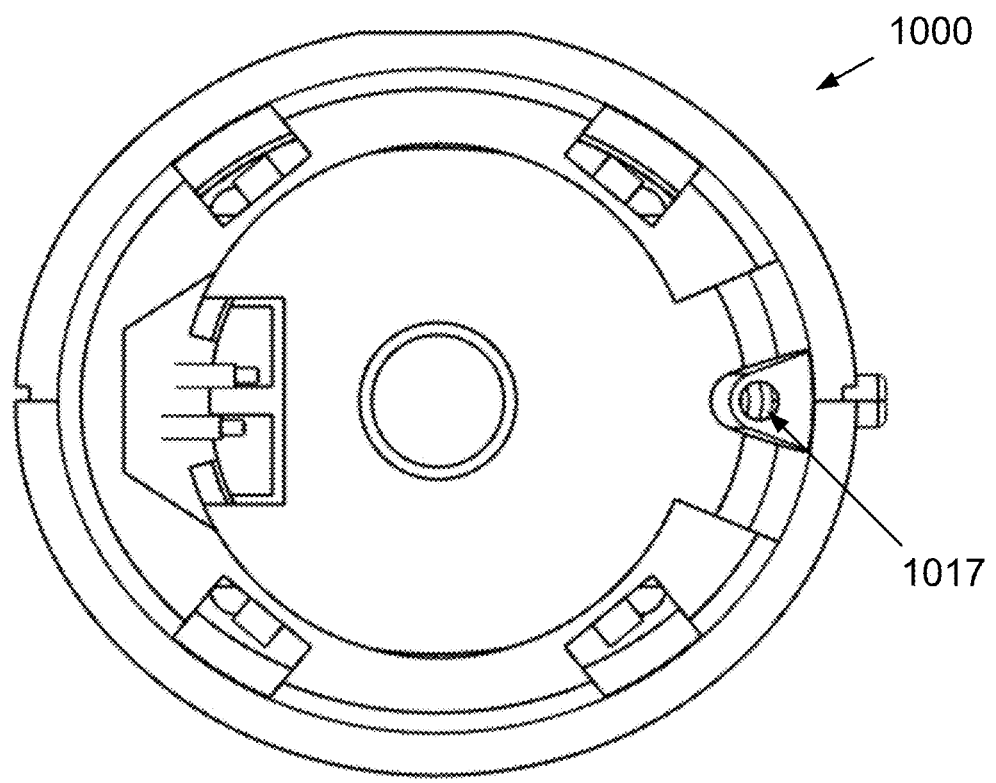

FIG. 27 is the view of the electronic device 1000 of FIG. 26, wherein the mouthpiece 1010 is omitted.

Figure 28:
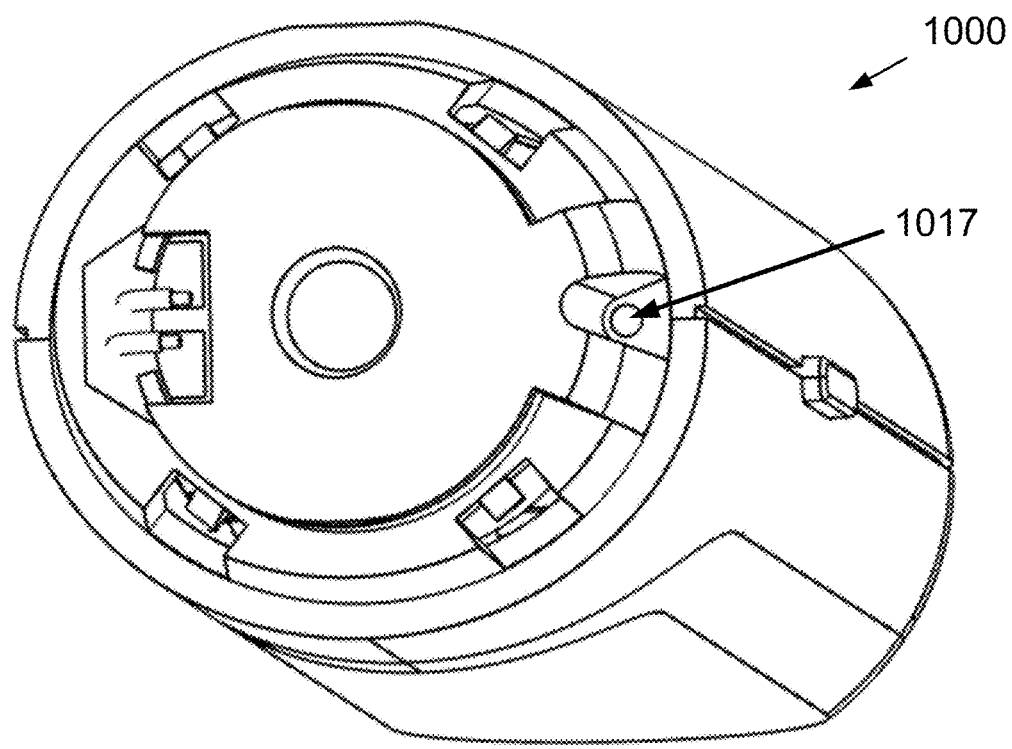

FIG. 28 is a perspective view of the electronic device 1000 of FIG. 27, wherein the mouthpiece 1010 is omitted.

Figure 29:
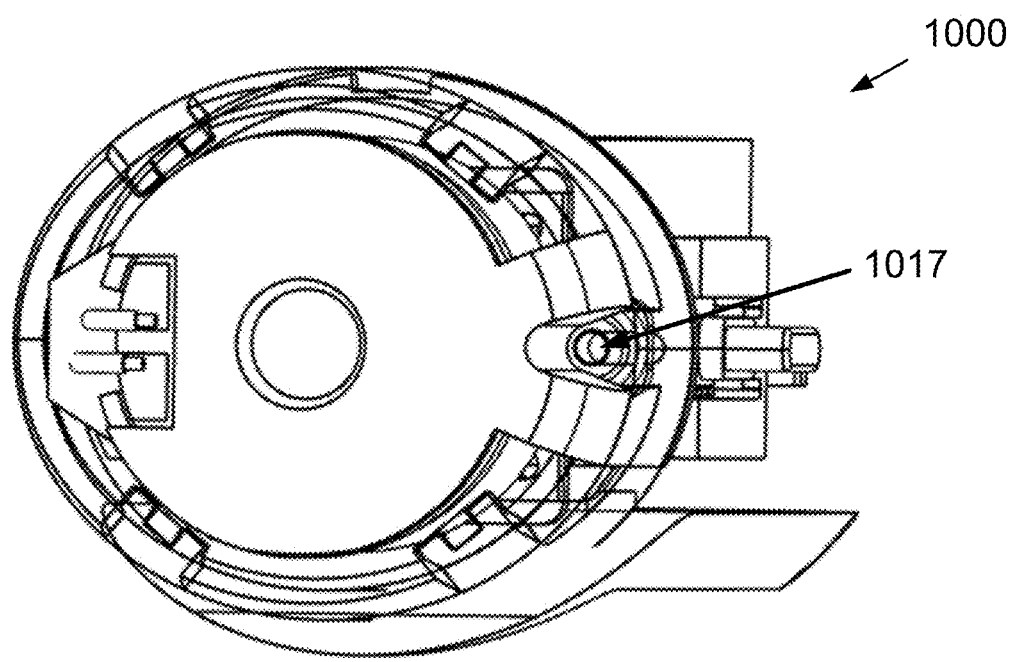
Figure 30:
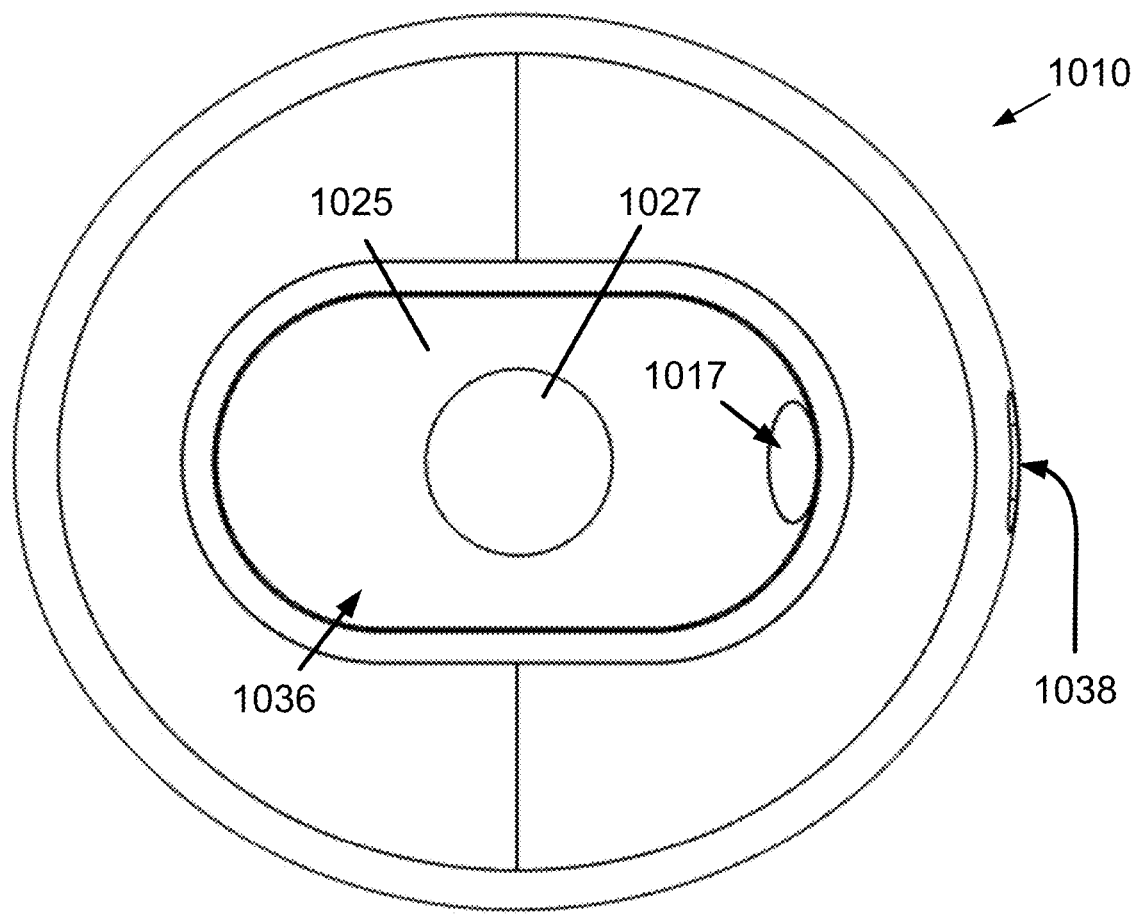
Figure 31:
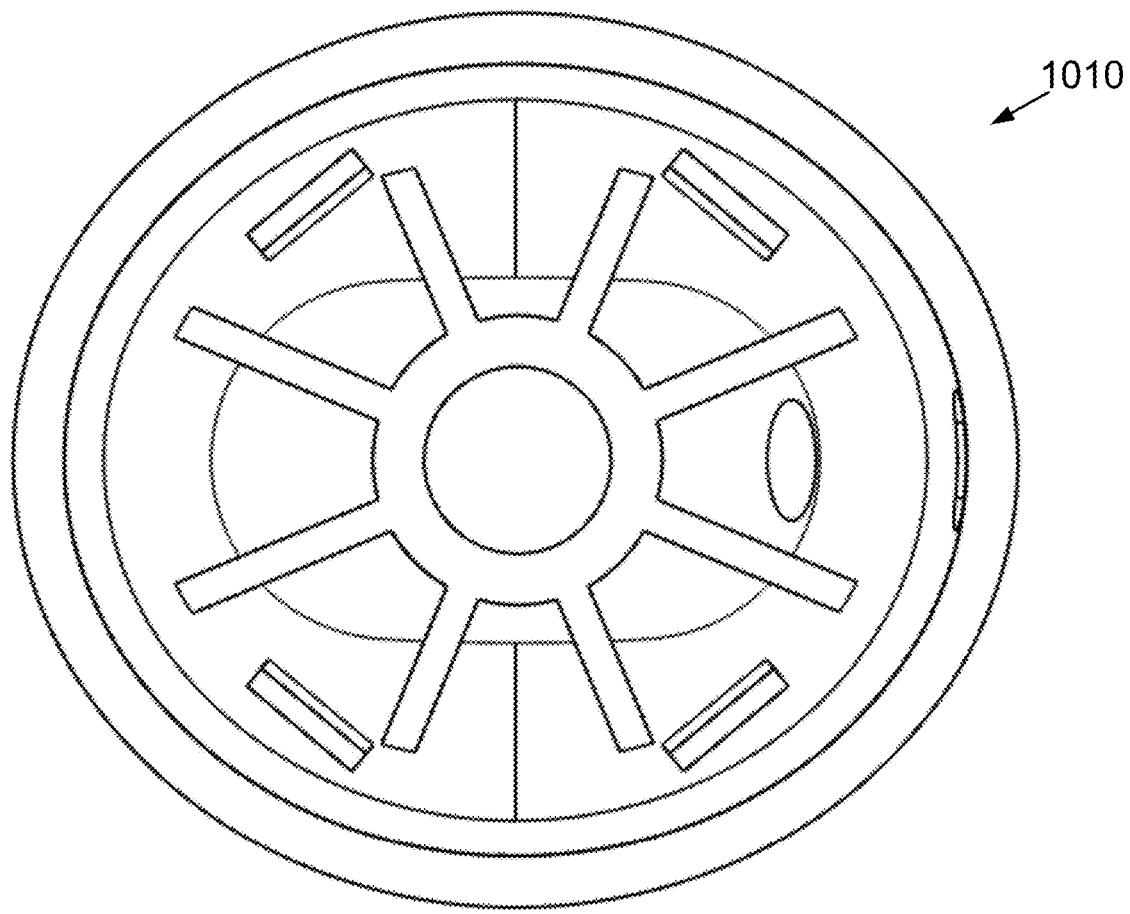
Figure 32:
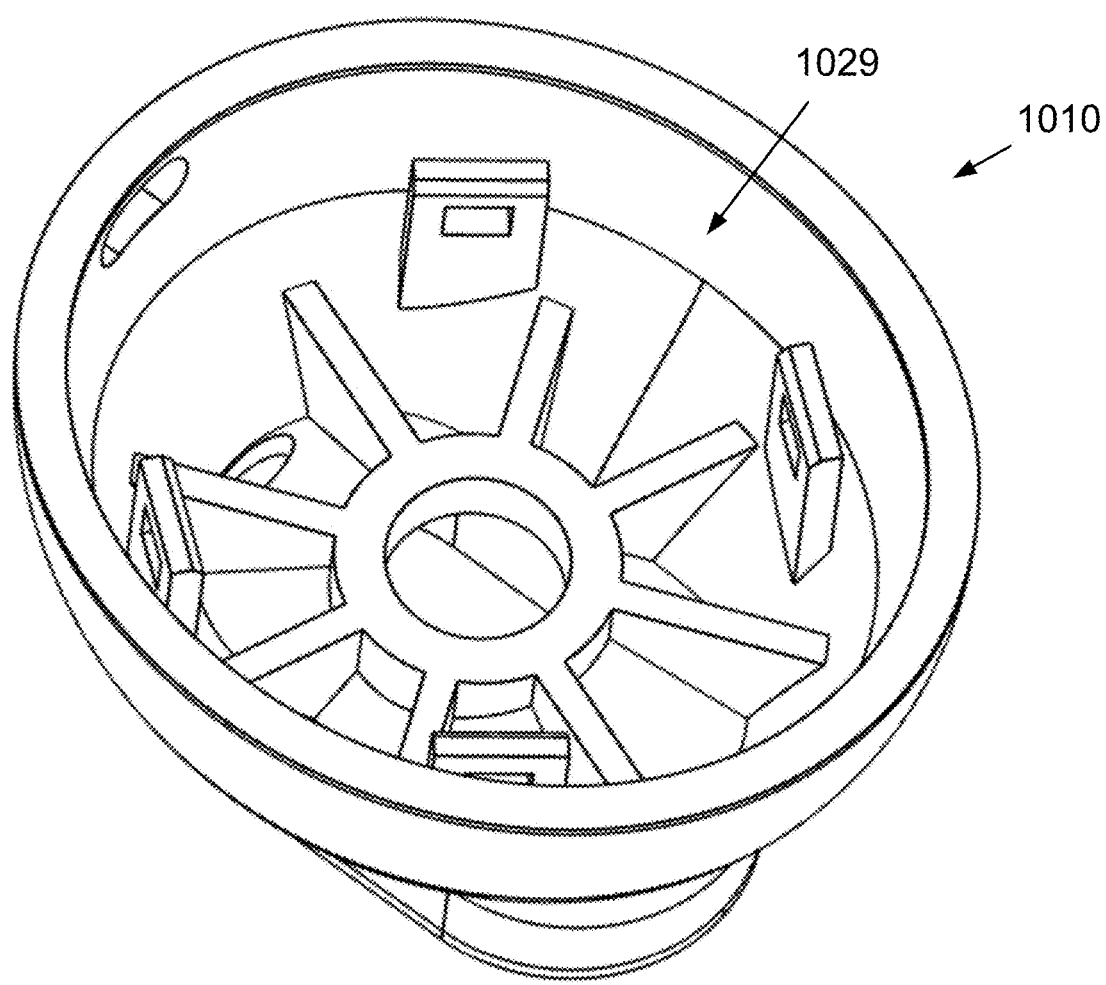
Figure 34:
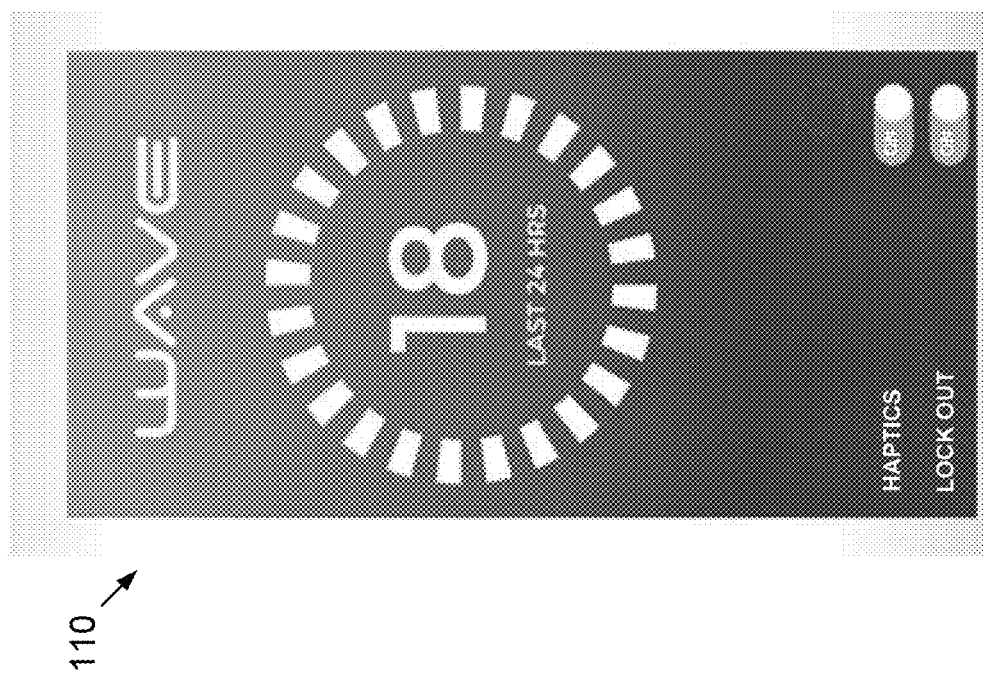

FIG. 29 is a perspective view of the electronic device 1000 of FIG. 27, wherein additional components are omitted and a lower body of the cartridge assembly 1004 is shown in transparent view for purposes of illustrated the diaphragm 1012 of the handheld base assembly 1002.

FIG. 30 is a top plan view of the mouthpiece 1010 of the cartridge assembly 1004. FIG. 30 shows mouthpiece opening 1036, the channel defining the air passageway 1017 in the cartridge body, the port 1038 for venting the interior area 1029 (see FIG. 32) of the mouthpiece 1010 from which the aerosolized liquid is suctioned, the mesh 1027, and the piezo 1025.

FIG. 31 is a bottom plan view of the mouthpiece 1010 of the cartridge assembly 1004.

FIG. 32 is a bottom perspective view of the mouthpiece 1010 of the cartridge assembly 1004.

FIG. 33 discloses software flow for firmware of the electronic device 100 similar to that described above but with some variations and represents an alternative implementation. Some preferred names for software functions and classes are set forth in FIG. 33.

FIGS. 34-44 illustrates various user interface screens 110, 111, 112, 113, 114, 115, 116, 117, 118, 119, and 120 for an app that is installed and run on a smartphone, such as an iPhone or an Android device, and which app communicates with the electronic device 100—and specifically with the handheld base assembly 102 of the electronic device 100—wirelessly using a protocol such as Bluetooth or Wi-Fi.

In particular, the user interface 110 of FIG. 34 shows a number of doses dispensed within the last twenty-four hours. The user interface 110 further includes two user settings (changeable via toggles): one for enabling or disabling vibrations generated by the haptic engine during aerosolizing; and one for locking the electronic device so that it cannot be used.

Figures 35, 36, 37:
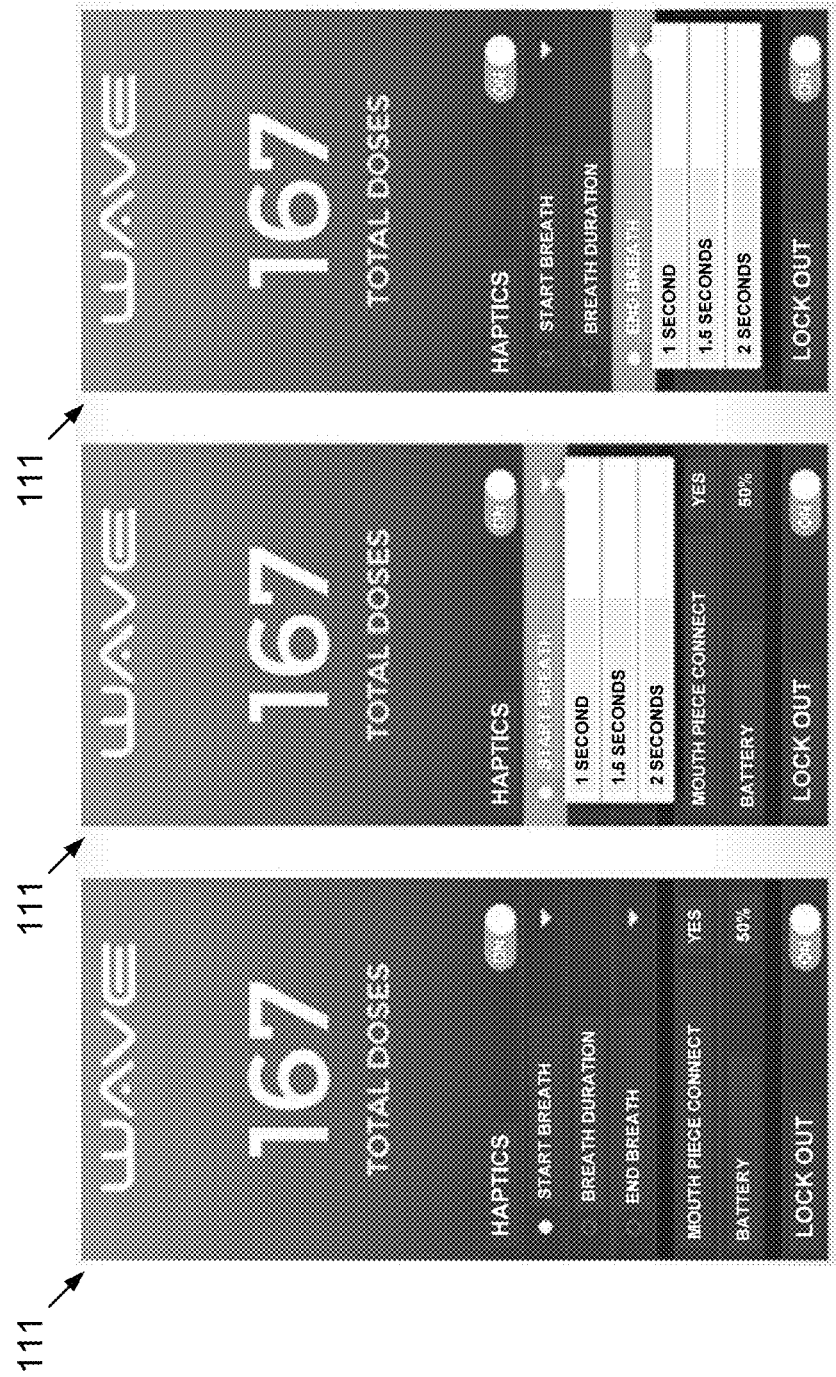

User interface 111 of FIG. 35 shows the total number of doses dispensed, settings for enabling/disabling the haptic engine and for locking the device. The user interface 111 also includes expandable menus relating to "Start Breath" settings; "Breath Duration" settings; and "End Breath" settings, as illustrated in FIGS. 36 and 37. The battery level and whether the cartridge is connected also are indicated.

User interface 112 of FIGS. 38-40 are similar to user interface 111 but include the ability to enable or disable additional devices (sees as device 1, device 2, and device 3).

User interface 113 of FIGS. 41-44 is similar to user interface 111, but is also scrollable for viewing settings (enable/disable) for additional devices.

User interface 114 of FIG. 43 shows current settings with expandable/dropdown menus for changing those settings.

User interface 115 of FIG. 44 shows scanning that is occurring for devices within range for connection with the app and is shown upon selection of "Find New Device" in user interface 114.

Figure 45:
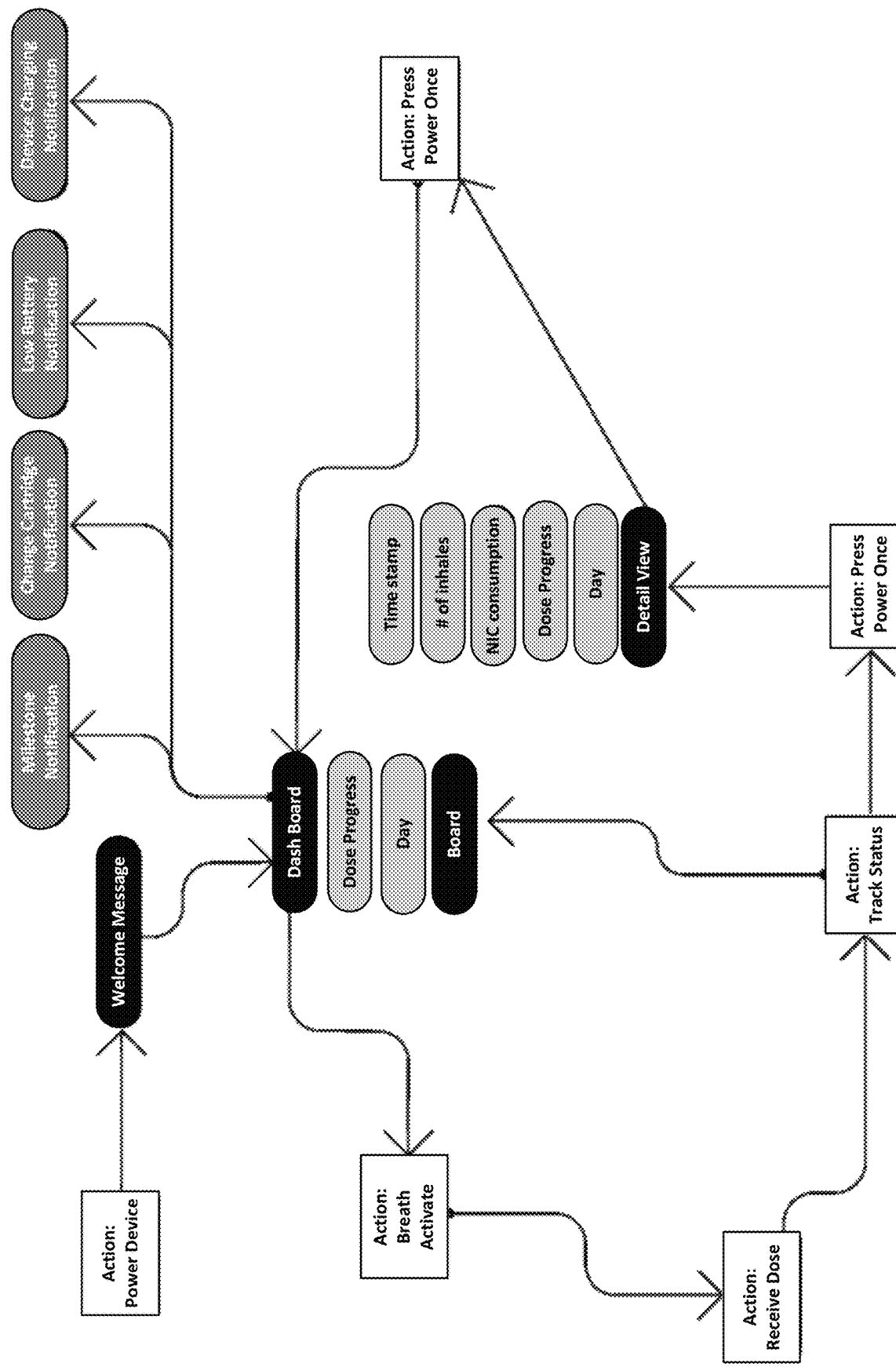

FIG. 45 illustrates possible user experiences when interacting with GUIs of the software in accordance with one or more aspects and features of the invention, which GUIs and sequences thereof are intended to drive adherence and compliance with prescribed medication use.

Figure 46:
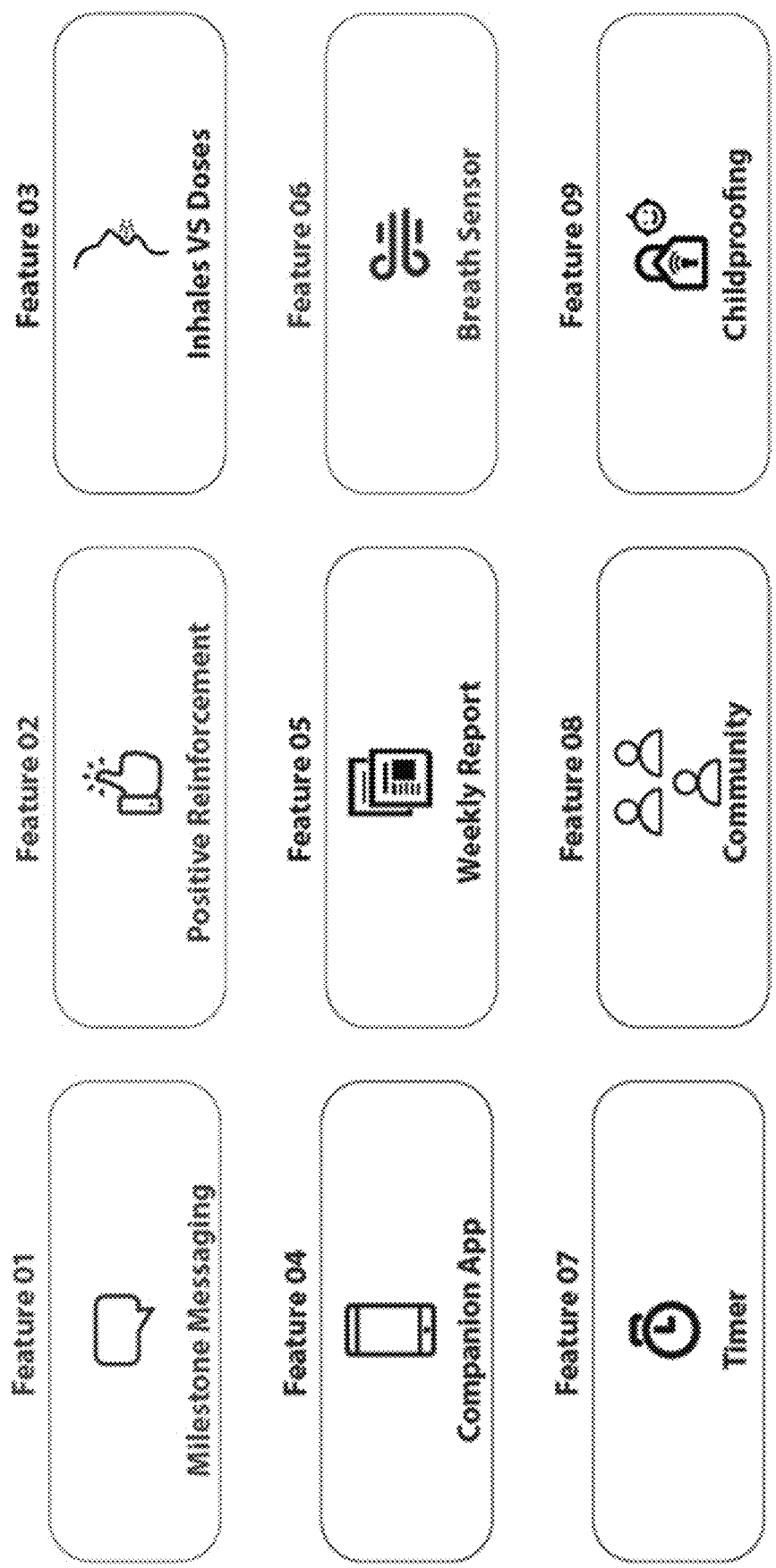

FIG. 46 illustrates features and capabilities of the software in accordance with one or more aspects and features of the invention, whether performed on the electronic device or on a mobile application on a smartphone, tablet device, or personal computer that is in communication with the electronic device.

It will be appreciated from the foregoing that in at least one embodiment, the electronic device comprises a handheld base assembly and a cartridge assembly, and that the cartridge assembly and the handheld base assembly are configured to removably couple together. The cartridge assembly preferably comprises a mouthpiece; a cartridge; and a bladder assembly as described in the incorporated disclosures.

Furthermore, the bladder assembly preferably comprises a bladder; a wick contained within the bladder; and a mesh assembly, wherein the mesh assembly preferably comprises a mesh material and a piezoelectric material, the mesh material being configured to vibrate when the piezoelectric material is actuated, whereby an aerosol is produced when the mesh material contacts a liquid of the bladder such that the aerosol may be inhaled through the mouthpiece. The handheld base assembly and cartridge assembly are configured magnetically to couple together and, specifically, the cartridge assembly magnetically mounts onto an end of the handheld base assembly.

In preferred embodiments, the cartridge assembly is disposable and eliminates potential patient misuse after its intended use. Moreover, because the vibrating mesh, ancillary aerosolizing components, and the liquid reservoir are all part of the disposable design, there is no maintenance or cleaning, and the device operates at optimal functionality.

The cartridge assembly also provides cartridge tracking, monitoring, user authentication, and geo-fencing capabilities for an increased standard of care and patient outcomes.

In use, the patient's inhalation triggers the vibrating mesh to activate under normal inspiratory use. A Bluetooth-enabled mobile app integration preferably is provided that logs precise dosing data in real-time, which is easily accessible by patient and clinician. The device is feature rich with visual indicators like a fully digital OLED display, and the smart cartridge ensures lifecycle, tamper-proof and chain of custody compliance from manufacture to delivery. The Bluetooth-enabled capabilities of the device further enables mobile application for compliance and precise dosing as well as accessible, real-time EMR data for providers, clinicians, and patients. In further facilitating precise dosing, customizable haptic vibration toggles, accessible via the mobile app, signal the end of the precisely metered dose.

Features of such preferred commercial embodiments include: no heat is used in the aerosolization and thus no HPHCs are produced; preferred commercial embodiments can be characterized as a breath actuated inhaler for all patient age groups; preferred commercial embodiments are ideal for thermo and pressure sensitive application programming interfaces ("APIs") and biologics; preferred commercial embodiments have local or systemic treatment capabilities; preferred commercial embodiments provide accurate and efficient metered dose delivery; and preferred commercial embodiment enable and facilitate subscription service, in-home delivery for continuity of care in chronic disease management.

Additional perceived benefits of aspects and features of the invention include: real-time data provided on screen; real-time data captured via mobile app; stored data in the electronic device; cost reduction for providers/insurers; predictive analytics; electronic-medical-record ("EMR") & health-insurance-portability-and-accountability-act ("HIPAA") compliant data; increase digital adherence & compliance (companion app & true digital therapeutics ("DTX")); gamification/digital prompts to encourage cessation and reduce misuse—indication area: nicotine reduction therapy ("NRT"); and gamification/digital prompts to encourage therapeutic adherence and reduce misuse—indication area: universal inhalation therapeutics.

Based on the foregoing description, it will be readily understood by those persons skilled in the art that the invention has broad utility and application. Many embodiments and adaptations of the invention other than those specifically described herein, as well as many variations, modifications, and equivalent arrangements, will be apparent from or reasonably suggested by the invention and the foregoing descriptions thereof, without departing from the substance or scope of the invention.

For example, it is recognized that the path of the aerosolized liquid through the electronic device is defined solely within the cartridge assembly, which does not include either the power source (battery) or the electronic circuitry (processor/firmware/transceiver), with the possible exception of a non-transient computer readable medium that preferably is located adjacent a bottom of the cartridge assembly if included. Because of this innovative aspect, i.e., because the electronics and power components are excluded and isolated from the airpath, being located in a separate and removable assembly of the electronic device, the possibility of airpath toxicity is reduced.

Accordingly, while the invention has been described herein in detail in relation to one or more preferred embodiments, it is to be understood that this disclosure is only illustrative and exemplary of the invention and is made merely for the purpose of providing a full and enabling disclosure of the invention. The foregoing disclosure is not intended to be construed to limit the invention or otherwise exclude any such other embodiments, adaptations, variations, modifications or equivalent arrangements, the invention being limited only by the claims appended hereto and the equivalents thereof.

What is claimed is:

1. An electronic device for producing an aerosol for inhalation by a person, comprising:

(a) a cartridge assembly configured to aerosolize a liquid to produce the aerosol for inhalation, the cartridge assembly comprising a memory, a mouthpiece, a liquid reservoir, and a mesh assembly comprising a mesh material and a piezoelectric material; and (b) a handheld base assembly removably coupled with the cartridge assembly, the handheld base assembly comprising a pressure sensor and circuitry including a processor or microcontroller and firmware executed by the processor or microcontroller for actuating the mesh assembly, the processor or microcontroller being configured to read the memory of the cartridge assembly;

(c) wherein the electronic device is configured to turn on when a button on an exterior of the electronic device is depressed for a predetermined period of time; and (d) wherein the cartridge assembly and the handheld base assembly collectively define an enclosed interior air passageway in fluid communication with the mesh material and extending between an interior space of the mouthpiece to a diaphragm arranged proximate the pressure sensor within the handheld base assembly, by which diaphragm a change in pressure in the enclosed interior air passageway is detected by the pressure sensor when a breath is drawn from the mouthpiece and the electronic device is turned on to consequently cause aerosolization.

2. The electronic device of claim 1, wherein no electronic components of the electronic device are exposed to the enclosed interior air passageway.

3. The electronic device of claim 2, wherein all components defining the enclosed interior air passageway are made from medical grade materials such that the electronic device is compliant with ISO 18562 and ISO 10993 standards.

* * * * *

UNITED STATES PATENT AND TRADEMARK OFFICE
CERTIFICATE OF CORRECTION

| | |
|---|---|
| PATENT NO. | : 11,925,207 B2 |
| APPLICATION NO. | : 18/237396 |
| DATED | : March 12, 2024 |
| INVENTOR(S) | : Mario Danek et al. |

It is certified that error appears in the above-identified patent and that said Letters Patent is hereby corrected as shown below:

In the Specification

At Column 15, Line 13, at the end of the line, delete "light-".

At Column 15, Line 14, at the beginning of the line, delete "emitting diode" and insert --liquid crystal display--.

Signed and Sealed this
Twenty-first Day of May, 2024

*Katherine Kelly Vidal*

Katherine Kelly Vidal
*Director of the United States Patent and Trademark Office*